US007749485B2

(12) United States Patent
Tournier et al.

(10) Patent No.: US 7,749,485 B2
(45) Date of Patent: Jul. 6, 2010

(54) LIPOSOMAL ASSEMBLY FOR THERAPEUTIC AND/OR DIAGNOSTIC USE

(75) Inventors: Herve Tournier, Valleiry (FR); Roland Hyacinthe, Armoy (FR); Michel Schneider, Troinex (FR)

(73) Assignee: Bracco Research S.A., Plan-les-Ouates (CH)

( * ) Notice: Subject to any disclaimer, the term of this patent is extended or adjusted under 35 U.S.C. 154(b) by 681 days.

(21) Appl. No.: 11/596,447

(22) PCT Filed: May 31, 2005

(86) PCT No.: PCT/EP2005/052482

§ 371 (c)(1),
(2), (4) Date: Nov. 13, 2006

(87) PCT Pub. No.: WO2005/117832

PCT Pub. Date: Dec. 15, 2005

(65) Prior Publication Data

US 2007/0196284 A1  Aug. 23, 2007

(30) Foreign Application Priority Data

Jun. 3, 2004  (EP) .................................. 04013141

(51) Int. Cl.
*A61K 51/00* (2006.01)
*A61M 36/14* (2006.01)
*B32B 5/16* (2006.01)
*B01F 3/00* (2006.01)

(52) U.S. Cl. ..................... 424/1.21; 428/402; 516/9; 977/907

(58) Field of Classification Search ....................... None
See application file for complete search history.

(56) References Cited

U.S. PATENT DOCUMENTS

| | | | |
|---|---|---|---|
| 4,920,016 A | 4/1990 | Allen | |
| 5,387,410 A | 2/1995 | Bosworth | |
| 5,716,673 A * | 2/1998 | Yen et al. ..................... | 427/240 |
| 5,827,533 A | 10/1998 | Needham | |
| 5,833,948 A | 11/1998 | Tournier | |
| 6,139,819 A | 10/2000 | Unger | |
| 6,143,321 A | 11/2000 | Needham | |
| 6,217,849 B1 | 4/2001 | Tournier | |
| 6,342,598 B1 | 1/2002 | Anelli | |
| 6,652,834 B2 | 11/2003 | Anelli | |
| 2002/0035217 A1 | 3/2002 | Uhrich | |

FOREIGN PATENT DOCUMENTS

| | | |
|---|---|---|
| EP | 0354855 B1 | 12/1994 |
| EP | 0804251 B1 | 9/2002 |
| WO | WO 92/10166 A1 | 6/1992 |
| WO | WO 98/18501 A2 | 5/1998 |
| WO | WO 99/55383 A2 | 11/1999 |
| WO | WO 02/055544 A2 | 7/2002 |
| WO | WO 03/074005 A2 | 9/2003 |
| WO | WO 03/084574 A1 | 10/2003 |

OTHER PUBLICATIONS

Alexander, Andrew L. et al: "Intracranial Black-Blood MR Angiography With High-Resolution 3D Fast Spin Echo", Magnetic Resonance in Medicine, 1998, pp. 298-310, vol. 40, Williams & Wilkins.
Edelman, Robert R. et al: "Extracranial Carotid Arteries: Evaluation With 'Black Blood' MR Angiography[1]", Radiology, Oct. 1990, pp. 45-50, vol. 177(1).
Golman, Klaes et al: "Molecular Imaging With Endogenous Substances" PNAS (Proceedings of the National Academy of Sciences of the USA), Sep. 2, 2003, pp. 10435-10439, vol. 100 No. 18.
Goodrich, K. Craig BS et al: "A Quantitative Study of Ramped Radio Frequency, Magnetization Transfer, and Slab Thickness in Three-Dimensional Time-of-Flight Magnetic Resonance Angiography in a Patient Population", Investigative Radiology, Jun. 1996, pp. 323-332, vol. 31(6), Lippincott-Raven Publishers.
Johansson, E. et al: "Cerebral Perfusion Assessment by Bolus Tracking Using Hyperpolarized $^{13}$C", Magnetic Resonance in Medicine, 2004, pp. 464-472, vol. 51, Wiley InterScience.
Kabalka, G.W. et al: "Gadolinium-Labeled Liposomes Containing Paramagnetic Amphipathic Agents: Targeted MRI Contrast Agents for the Liver", Magnetic Resonance In Medicine, 1988, pp. 89-95, vol. 8, Academic Press, Inc.
Macdonald, Robert C. et al (prepared by): "O-Ethylphosphatidylcholine: A Metabolizable Cationic Phospholipid Which Is a Serum-Compatible DNA Transfection Agent", Journal of Pharmaceutical Sciences, Sep. 1999, pp. 896-904, vol. 88, No. 9.
Malmstem, M: "Liposomes", Surfactants and Polymers in Drug Delivery, 2002, Ch.4, pp. 87-131, Marcel Dekker Inc.
New, Roger R. C. (edited by): "Preparation Of Liposomes", 1989, pp. 33-104, Oxford University Press.
Nicolazzi, Celine et al: "Anionic Polyethyleneglycol Lipids Added to Cationic Lipoplexes Increase Their Plasmatic Circulation Time", Journal of Controlled Release, 2003, pp. 429-443, vol. 88, XP004414814, Elsevier Science B.V.
Torchilin, V.P. et al: "Amphiphilip poly-N-vinylpyrroilidones: synthesis, properties and liposome surface modification", Biomaterials, 2001, pp. 3035-3044, vol. 22, XP004301382, Elsevier Science Ltd.
Yamamoto, Yuji et al: "Long-circulating poly(ethylene glycol)=poly(D,L-lactide) block copolymer micelles with modulated surface charge", Journal of Controlled Release, 2001, pp. 27-38, vol. 77, XP004311660, Elsevier Science, B.V., Amsterdam.
PCT International Search Report, mail date Oct. 6, 2005, PCT/EP05/05248, Bracco Research.
PCT Written Opinion of the International Searching Authority, mail date Oct. 6, 2005, PCT/EP05/05248, Bracco Research.

\* cited by examiner

*Primary Examiner*—Robert M Kelly
(74) *Attorney, Agent, or Firm*—M. Caragh Noone

(57) ABSTRACT

Composition for diagnostic or therapeutic use which comprises an assembly comprising an active agent. The assembly comprises a liposome and a plurality of micellar components associated thereto, said micellar components being associated to the outer surface of the envelope of said liposome through a substantially electrostatic interaction, When an active compound is incorporated into the micelles, a substantial amount of said active compound can be linked to a singe liposome. Furthermore, the presence of the outer micellar layer allows to increase the residence time of said liposome in the blood stream.

17 Claims, 4 Drawing Sheets

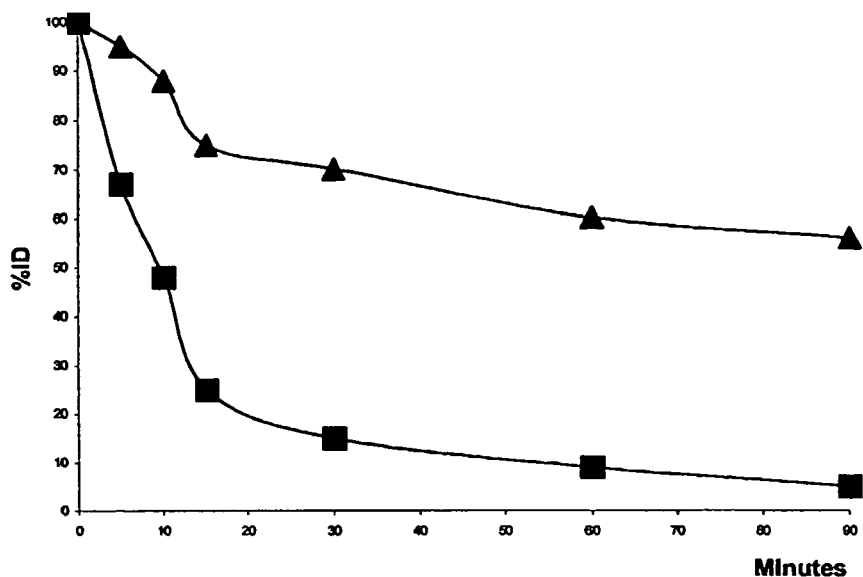
Fig 6
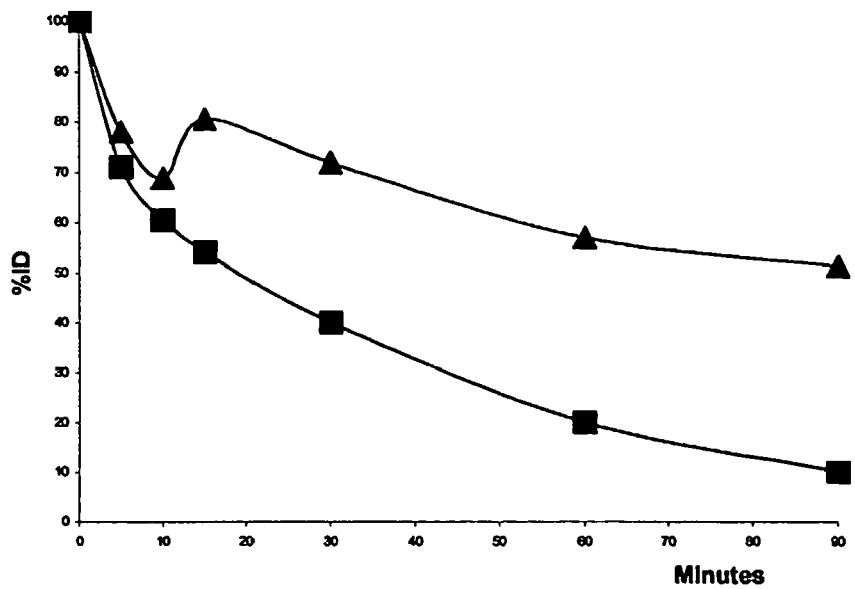
Fig. 7
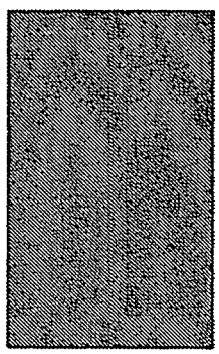 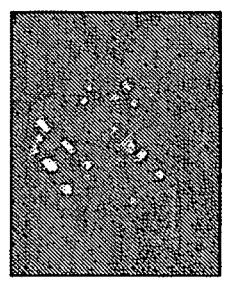
Fig. 8a    Fig. 8b

LIPOSOMAL ASSEMBLY FOR THERAPEUTIC AND/OR DIAGNOSTIC USE

This application is the national stage application of corresponding international application number PCT/EP2005/052482 filed May 31, 2005, which claims priority to and the benefit of the European application no. 04013141.9, filed Jun. 3, 2004, all of which are hereby incorporated by reference.

FIELD OF THE INVENTION

The present invention relates to a new liposomal composition containing an active agent for therapeutic and/or diagnostic use, to a manufacturing method thereof and to a pharmaceutical kit comprising said composition. The invention further relates to a method for increasing the amount of an active agent associable to a liposome and to a method for increasing the residence time of liposomal vesicles in the blood circulation. In particular, the present invention can find advantageous applications in the field of Magnetic Resonance Imaging (MRI).

BACKGROUND OF THE INVENTION

Liposomes are well known in the therapeutic or diagnostic field as suitable carriers for active agents, such as therapeutic and/or diagnostic compounds. Various liposome-based compositions containing active agents have been proposed, particularly for those agents showing a reduced half-life in the blood stream. For instance, U.S. Pat. No. 6,143,321 discloses liposomes containing a micellar preparation entrapped in the interior space thereof, said micellar preparation comprising an active agent aggregated with a lipid surfactant to form a micelle.

Diagnostic imaging employing agents capable of enhancing the images obtainable with different imaging techniques (known as "contrast agents" or "image enhancing agents") has also become a rather widely adopted practice.

For instance, iodinated products, such as Iopamidol® or Iomeprol® (Bracco Imaging S.p.A.), are widely employed in X-ray contrast analysis, in particular computer tomography (Cr) X-ray, whilst compounds containing paramagnetic ions such as ProHance® or MultiHance® (Bracco Imaging), are widely employed in MRI analysis.

Among the various properties of an image enhancing agent, some of those which are probably more desirable are a high image enhancing capability and a sufficiently long residence time thereof in the relevant system, tissue or organ to be visualized. Many efforts have thus been dedicated in the past to improve these two properties of contrast agents.

For instance, U.S. Pat. No. 6,217,849 discloses aqueous suspension of liposomes for x-ray or NMR imaging having improved capability of remaining in the blood circulation.

U.S. Pat. No. 5,387,410 suggests using a liposome to carry a paramagnetic ion chelate within or outside the external surface thereof, in order to obtain an enhanced NMR imaging of a selected organ.

U.S. Pat. No. 5,833,948 teaches to incorporate paramagnetic ion chelates into micellar structures comprising a non-ionic surfactant, to improve the blood-pool properties thereof.

U.S. Pat. No. 5,756,069 relates to the problem of increasing the concentration of a MRI responsive agent on carriers, such as liposomes, to provide a useful image. Polychelating compounds are disclosed which are capable of binding a plurality of paramagnetic ions and comprising a lipid-soluble anchor to bound the compound to a liposome or a micelle.

Furthermore, image enhancing compounds can also be used in combination with targeting compounds (which allow to link the image enhancing compound to a specific target site—e.g. a tissue, an organ or specific cells—in order to selectively enhance the imaging thereof) and/or with therapeutic agents (e.g. which can be released at a corresponding site, tissue or organ upon visualization thereof).

SUMMARY OF THE INVENTION

The applicant has now found a new assembly for diagnostic and/or therapeutic use where a plurality of micelles can be associated to the outer surface of a liposome. The association is effected through a substantially electrostatic interaction. With this new assembly, it is possible either to link a substantial amount of an active compound to a single liposome, to increase the residence time of said liposome in the blood stream or, according to a preferred aspect of the invention, to obtain a contrast agent with enhanced imaging properties and prolonged blood circulation.

A first aspect of the invention thus relates to a composition for diagnostic or therapeutic use which comprises an assembly bearing an active agent, wherein said assembly comprises:
a liposome having a boundary envelope with a respective inner and an outer surface, said envelope defining an internal portion thereof; and
a plurality of micellar components associated to the outer surface of the envelope of said liposome, wherein said micellar components are associated to said liposome through a substantially electrostatic interaction.

According to a preferred embodiment, said liposome bears a first overall net charge and said plurality of micellar components bear a second overall net charge opposite in sign to said first net charge.

According to the present invention, the term "active agent" includes within its meanings any therapeutic or diagnostic agent as defined in the following of this specification. Said active agent can be associated to the liposome (e.g. dissolved or dispersed in the internal aqueous phase and/or incorporated in the boundary envelope), to the micelles (e.g. as a micelle forming compound) or to both.

When referred to an assembly of the invention, the term "substantially electrostatic interaction" means that the main interaction capable of stably associating the liposome and the micelles is the electrostatic (or ionic) interaction determined by the opposite negative and positive charges on the respective two components.

The Applicant has in particular observed that the presence of specific compounds in the micellar component may allow to substantially increase the residence time of liposomes associated to said micelles in the blood stream. According to a preferred embodiment, said micellar component comprises an amphiphilic polymeric compound. Preferably said amphiphilic polymeric compound is a polymeric surfactant or a phospholipid bearing a hydrophilic polymeric moiety. Alternatively, or in addition thereto, said micellar component.; may comprise bile acids or derivatives thereof, or lysophospholipids.

A further aspect of the invention relates to a method for conferring prolonged blood circulation properties to a liposome comprising a lipid envelope, said method comprising associating to an outer portion of said lipid envelope a micellar component comprising amphiphilic polymeric compound.

The Applicant has further observed that it is possible to substantially increase the amount of an active agent when a micellar component containing said active agent is associated to a liposome in an assembly of the invention. This is of particular interest when the assembly is linked to a targeting site, where it may thus locally bring an increased amount of active agent.

An advantageous application of this finding is the enhancement of the imaging response of an image enhancing compound (e.g. an MRI responsive compound, for instance a gadolinium chelate), by employing an assembly wherein the micelles include said image enhancing compound, in particular when the image enhancing component is associated with a targeting ligand, which targets a specific biological or pathological site. For instance, it has been determined that micelles containing a lipidic gadolinium complex typically contain about 500 Gd atoms. Thus, a micelle containing a targeting agent may provide at most 500 Gd atoms for image enhancement when bound to a respective targeted site. On the other hand, the applicant has observed that at least about 5000 micelles can be associated to the external surface of a 1 μm diameter liposome to form an assembly; thus, when said assembly is bound to the same targeted site, it will associate something like about 2,500,000 (500×5000) Gd atoms to a single target site, which is clearly a substantially higher amount than the number of Gd atoms associable to the same target site by a single micelle.

A preferred aspect of the invention thus relates to a composition as above defined wherein the active agent is comprised in the micellar component.

Preferably, said active agent is an image enhancing compound, more preferably a MRI responsive compound, in particular a paramagnetic metal ion.

In a preferred embodiment, said assembly further comprises a targeting ligand, preferably included in the micellar component. In a further preferred embodiment an active agent is also included in the liposome.

FIGURES

FIGS. 5-7 are graphs comparing the blood circulation of assemblies of the invention with respect to liposomes;

FIGS. 8a and 8b are images of in vitro assays.

DETAILED DESCRIPTION OF THE INVENTION

Figure 1:
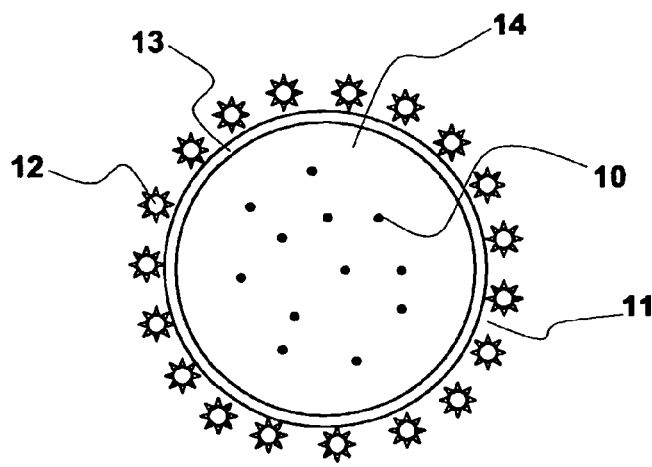
FIGS. 1, 1a and 1b are schematic representations of an assembly of the invention and of the respective components thereof.
Figure 1A:
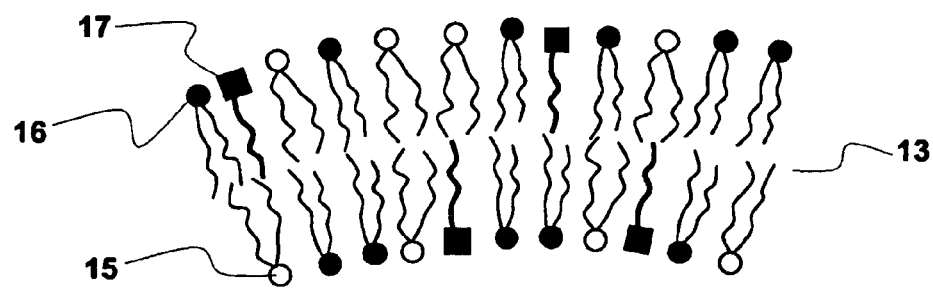
Figure 1B:
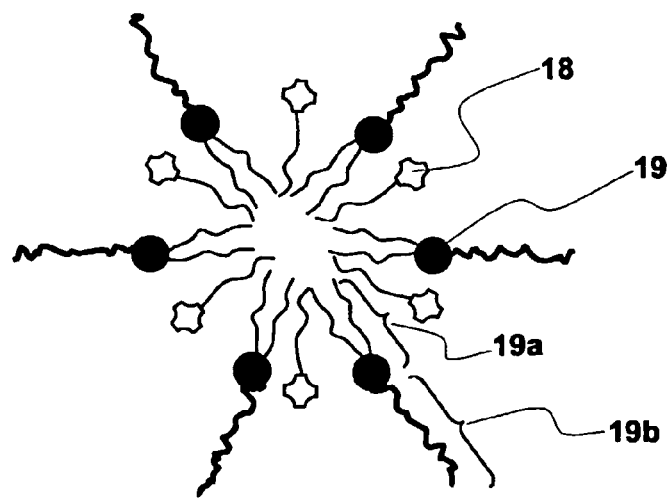

FIG. 1 shows a schematic cross-sectional representation of an assembly according to the invention. Said assembly comprises a liposome (11) of substantially spherical form associated to a plurality of micelles (12), and immersed in a suitable physiologically acceptable liquid carrier (e.g. saline solution). The liposome comprises a lipid envelope (13) which defines the internal liquid-filled portion (14) thereof, which may optionally comprise an active agent (10). FIG. 1a shows a portion of the liposomal envelope (13), which in this specific embodiment is formed by a lipid bilayer. In said embodiment, the lipids forming the envelope are neutral phospholipids (15), positively charged phospholipids (16) and cholesterol (17). The micelle illustrated in the specific embodiment of FIG. 1b comprises an amphiphilic complex of a paramagnetic ion (18), e.g. Gd, and a negatively charged amphiphilic material (19), e.g. a phosphatidylethanolamine (19a) linked to a polyethyleneglycol moiety (19b).

Liposomes

The term liposome includes within its meaning substantially spherical aggregations of amphiphilic compounds, including lipid compounds, typically in the form of one or more concentric layers. As known in the art, amphiphilic compounds are those molecules having a hydrophilic polar head (e.g. a polar or ionic group) and a hydrophobic organic tail (e.g. a hydrocarbon chain). These compounds are generally also classified as surfactants, emulsifying agents or dispersing agents in the art.

Liposomes are typically formed in aqueous suspensions and contain at least one bilayer of an amphiphilic compound. The hydrophilic heads of the amphiphilic compounds forming the external layer of the bilayer are directed towards the exterior of the spherical structure, while the hydrophilic heads of the amphiphilic compounds forming the internal layer of the bilayer are directed towards the interior of said spherical structure. The liquid incorporated in the interior of the spherical structure of the liposomes is in general the same as the one of the aqueous suspension, optionally containing additional compounds which are not present (or are present to a lesser extent) in the outer aqueous suspension, such as an active agent. The liquid fills the internal volume of liposomes for the substantial totality of said volume, i.e. more than 90%, preferably more than 95% and typically for about 100%.

Preferred materials for preparing liposomes are phospholipids, optionally in admixture with other amphiphilic compounds. Phospholipids are amphiphilic compounds which typically contain at least one phosphate group and at least one, preferably two, lipophilic long-chain hydrocarbon group.

Examples of suitable phospholipids include esters of glycerol with one or preferably two (equal or different) residues of fatty adds and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic add are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine or of sphingomyelin. Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroylphosphatidylglycerol (DLPG) and its alkali metal salts, diarachidoylphosphatidylglycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoylphosphatidylethanolamine (DMPE), dipalmitoylphosphatidylethanolamine (DPPE), distearoyl phosphatidyl-ethanolamine (DSPE), dioleylphosphatidylethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

The term phospholipid further includes modified phospholipid, e.g. phospholipids where the hydrophilic group is in turn bound to another hydrophilic group. Examples of modified phospholipids are phosphatidylethanolamines modified with polyethylenglycol (PEG), i.e. phosphatidylethanolamines where the hydrophilic ethanolamine moiety is linked to a PEG molecule of variable molecular weight (e.g. from 300 to 5000 daltons), such as DPPE-PEG (or DSPE-PEG), i.e. DPPE (or DSPE) having a PEG polymer attached thereto. For example, DPPE-PEG2000 refers to DPPE having attached thereto a PEG polymer having a mean average molecular weight of about 2000.

Mixtures of phospholipids can also be used, such as, for instance, mixtures of DPPC, DSPC and/or DAPC with DSPS, DPPS, DSPA, DPPA, DSPG, DPPG, Ethyl-DSPC and/or Ethyl-DPPC, The phospholipid is typically the main component of the liposomal envelope, amounting to at least 50% (w/w) of the total amount of components forming said envelope. In some preferred embodiments, substantially the totality of the envelope (i.e. at least 90% and up to 100% by weight) can be formed of phospholipids.

The phospholipids can conveniently be used in admixture with other amphiphilic compounds such as, for instance, fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic adds including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate,; long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methylamino) octadecanoic acid; N-[12-(((7'-diethylaminocoumarin-3-yl) carbonyl)methylamino)-octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N, N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

Preferred additional compounds are lipids including cholesterol, ergosterol, phytosterol, sitosterol, lanosterol, tocopherol, propyl gallate or ascorbyl palmitate; fatty acids such as myristic acid, palmitic acid, stearic acid, arachidic acid and salts and derivatives thereof; butylated hydroxytoluene; or mixtures thereof. Particularly preferred is cholesterol. These compounds can be added to the liposome forming composition in an amount of up to about to 60% by mole of the total composition, preferably up to about 25%.

In order to confer the desired overall net charge to the liposome, the respective envelope comprises at least one component bearing an overall net charge, in particular a charged amphiphilic material, preferably a lipid or a phospholipid.

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DMPE-PEG2000, DMPE-PEG3000, DMPE-PEG4000, DPPE-PEG5000, DPPE-PEG2000, DPPE-PEG3000, DPPE-PEG4000, DPPE-PEG5000, DSPE-PEG2000, DSPE-PEG3000, DSPE-PEG4000, DSPE-PEG5000, DAPE-PEG2000, DAPE-PEG3000, DAPE-PEG4000 or DAPE-PEG5000 can be used as negatively charged molecules. Also the lyso-form of the above cited phospholipids, such as lysophosphatidylserine derivatives (e.g. lyso-DMPS, -DPPS or -DSPS), lysophosphatidic add derivatives (e.g. lyso-DMPA, -DPPA or -DSPA) and lysophosphatidylglycerol derivatives (e.g. lyso-DMPG, -DPPG or -DSPG), can advantageously be used as negatively charged compound. Examples of negatively charged lipids are bile acid salts such as cholic acid salts, deoxycholic acid salts or glycocholic acid salts; and ($C_{12}$-$C_{24}$), preferably ($C_{14}$-$C_{22}$) fatty acid salts such as, for instance, palmitic acid salt, stearic acid salt, 1,2-dipalmitoyl-sn-3-succinylglycerol salt or 1,3-dipalmitoyl-2-succinylglycerol salt.

Preferably, the negatively charged compound is selected among DPPA, DPPS, DSPG, DSPE-PEG2000, DSPE-PEG5000 or mixtures thereof.

The negatively charged component is typically associated with a corresponding positive counter-ion, which can be mono- (e.g. an alkali metal or ammonium), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids bearing an overall positive charge are derivatives of ethylphosphatidylcholine, in particular di-esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC). The negative counterion is preferably an halogen ion, in particular chlorine or bromine. Examples of positively charged lipids are alkylammonium salts with a halogen counter ion (e.g. chlorine or bromine) comprising at least one ($C_{10}$-$C_{20}$), preferably ($C_{14}$-$C_{18}$), alkyl chain, such as, for instance mono or di-stearylammonium chloride, mono or di-hexadecylammonium chloride, dimethyldioctadecylammonium bromide (DDAB), hexadecyltrimethylammonium bromide (CrAB). Further examples of positively charged lipids are tertiary or quaternary ammonium salts with a halogen counter ion (e.g. chlorine or bromine) comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP).

DSEPC, DPEPC and/or DSTAP are preferably employed as positively charged compounds in the liposome envelope.

The positively charged component is typically associated with a corresponding negative counter-ion, which can be mono- (e.g. halogen), di- (e.g. sulphate) or tri-valent (e.g. phosphate). Preferably the counter-ion is selected among halogen ions, such as $F^-$ (fluorine), $Cl^-$ (chlorine) or $Br^-$ (bromine).

In order to allow an effective electrostatic interaction with the micelle, the total amount of charged compounds in the liposomal envelope is of at least 1% by mole with respect to the total amount of material forming said envelope, preferably of at least 5% and more preferably of at least 10% by mole. It has been observed that amounts of less than 80% by mole of charged compounds are in general sufficient to achieve an effective liposome-micelles interaction; preferably said amounts are not higher than about 75% by weight and more preferably not higher than about 60% by mole.

Mixtures of neutral and charged phospholipids and/or charged lipids can be satisfactorily employed to form the liposomes of an assembly of the present invention, optionally in admixture with other amphiphilic compounds. Preferably, mixtures of two or more lipids or phospholipids, at least one with a neutral charge and at least one with an overall net charge, are employed. More preferably, mixtures of two or more lipids or phospholipids, at least one with neutral and at least one with positive charge are employed, to obtain liposomes with an overall positive charge. Particularly preferred are mixtures of DSPC and/or DPPC with ethyl-DSPC, ethyl-DPPC and/or DSTAP.

Other excipients or additives may be present in the liposome-forming composition, without necessarily being involved (or being only partially involved) in the formation of the liposomal envelope. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars, and hydrophilic polymers like polyethylene glycol.

The liposomes of an assembly of the present invention may further contain an active agent, such as a therapeutic agent or a diagnostic agent. These compounds may either be associated to the lipid envelope of the liposome (e.g. incorporated into and/or bound thereto) and/or dissolved or dispersed (e.g. as a micellar dispersion) into the internal aqueous volume thereof. Although a targeting ligand may also be associated to the lipid envelope of the liposome, said compounds are nevertheless more advantageously associated to the micelles of the assembly, as explained in detailed hereinafter, in order to maximize the targeting effect thereof.

The term "therapeutic agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Therapeutic agents thus include any compound or material capable of being used in the treatment (including diagnosis, prevention, alleviation, pain relief or cure) of any pathological status in a patient (including malady, affliction, disease lesion or injury). Examples of therapeutic agents are drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmides. Among these, drugs or pharmaceuticals are preferred.

Examples of therapeutic agents include antiulcerants such as cimetidine, famotidine, ranitidine, roxatidine acetate, pantoprazole, omeprazole, lansoprazole or sucralfate; gut relaxants or prokinetics such as propantheline bromide, camylofin (acamylophenine), dicyclomine, hyoscine butyl bromide, mebeverine, cisapride, oxybutynin, pipenzolate methyl bromide, drotaverine, metoclopramide, clidinium bromide, isopropamide or oxyphenonium bromide; enzymes or carminatives, such as pancreatin, papain, pepsin, or amylase; hepatobiliary preparations such as chenodeoxycholic acid, ursodeoxycholic acid, L-ornithine or silymarin; antihypertensives such as clonidine, methyidopa, sodium nitroprusside, terazosin, doxazosin, (DI) hydralazine or prazosin; beta blockers such as esmolol, celiprolol, atenolol, labetolol, propranolol, metoprolol, carvedilol, sotalol, oxyprenolol or bisoprolol; calcium channel blockers such as felodipine, nitrendipine, nifedipine, benidipine, verapamil, amlodipine or lacidipine; ace inhibitors such as enalapril, lisinopril, ramipril, perindopril, benazepril or captopril; angiotensin II inhibitors such as losartan potassium; potassium channel activators, such as nicorandil; diuretics and antidiuretics such as hydrochlorothiazide, xipamide, bumetanide, amiloride, spironolactone, indapamide, triamterene, clopamide, furosemide or chlorthalidone; antianginals such as isoscorbide dinitrate, oxyfedrine, isosorbide 5-mononitrate, diltiazem, erythrityl tetranitrate, trimetazidine, lidoflazine, pentaerythritol tetranitrate, glyceryl trinitrate or dilazep; coagulants such as conjugated oestrogens, diosmin, menaphthone, menadione, haemocoagulase, ethamsylate (cydanamine), rutin·flavonoids or adrenochrome monosemicarbazone; anticoagulants antithrombotics or antiplatelets such as ticlopidine, warfarin, streptokinase, phenindione, rtpa, urokinase, vasopressin, nicoumalone, heparin, low molecular weight heparins, mucopolysaccharide polysulphate or dipyridamole; antiarrhythmics such as quinidine, disopyramide, procainamide, lignocaine (lidocaine), mexiletine, amiodarone, adenosine, propafenone; drugs in cardiac failure and shock such as mephentermine, digoxin, dopamine, dobutamine or noradrenaline, vasodilators such as isoxsuprine, xanthinol nicotinate, nylidrin HCl, pentoxifylline (oxpentifylline) or cyclandelate; cardiac glycosides such as deslaneside, digitoxin, digoxin or digitalin; penicillins such as benzyl penicillin, procaine penicillin (G), benzathine penicillin (G), phenoxymethyl penicillin, penicillin G/V, bacampicillin, carbenicillin, piperadllin, ampicillin (optionally in combination with sulbactam or probenecid), cloxacillin, or amoxycillin (optionally in combination with bromhexine, cloxacillin, carbocysteine or clavulanic acid); quinolones or fluoroquinolones such as nalidixic acid, pefloxacin, ofloxacin, sparfloxacin, norfloxacin, ciprofloxacin, lomefloxacin, cephalosporins such as ceftizoxime, cefumxime, cefixime, cefotaxime, cefaclor, ceftriaxone sodium, cefadroxil, cephalexin, (optionally in combination with bromhexine HCl or probenecid) cefazolin, cephaloridine, ceftazidime or ceforperazone; sulphonamides such as sulphonamides, sulphamoxole, sulphadimehtoxine, cotrifamole, cotrimoxazole, trimethoprim, aminoglycosides such as gentamicin, tobramycin, neomycin, amikacin, sisomicin, kanamycin, netilmicin, polymyxins such as polymyxin-b, colistin sulphate; chloramphenicol; tetracyclines such as tetracycline, doxycydine, minocycline, demeclocycline, oxytetracycline; macrolides such as erythromycin, (optionally in combination with bromhexine), clarithromycin, vancomycin, lincomycin, azithromycin, spiramycin, roxithromycin, clindamycin, cefpirome, teicoplanin (teichomycin a2), antivirals, such as abacavir, lamivudine, acyclovir, amantadine, interferon, ribavirin, stavurdine, lamivudine or zidovudine (azt); antimalarials, such as quinine, proguanil, chloroquine, primaquine, amodiaquine, artemether, artesunate, mefloquine, pyrimethamine, arteether, mepacrine; antituberculars such as cycloserine, capreomycin, ethionamide, prothionamide, isoniazid (inh), rifampicin, rifampicin optionally in combination with inh, isoniazide, pyrazinamide and/or ethambutol; ethambutol (optionally in combination with isoniazid), streptomycin or pyrazinamide; anthelmintics & antiinfestives such as piperazine, niclosamide, pyrantel pamoate, levamisole, diethyl carbamazine, tetramisole, albendazole, praziquantel, sodium antimony gluconate or membendazole; antileprotics such as dapsone or clofazimine; antianaerobics, antiprotozoals or antiamoebics such as tinidazole, metronidazole (optionally in combination with furazolidone or norfloxacin), diloxanide furoate, secnidazole, hydroxyquinolones, dehydroemetine, ornidazole or furazolidone; antifungals such as fluconazole, ketoconazole, hamycin, terbinafine, econazole, amphotericin-b, nystatin, clotrimazole, griseofulvin, miconazole or itraconazole; vitamins; respiratory stimulants such as doxapram hydrochloride; antiasthmatics such as isoprenaline, salbutamol(albuterol), orciprenaline, ephedrine, terbutaline sulphate, salmeterol, aminophylline, therophylline, beclomethasone dipropionate or fluticasone propionate; antiallergics such as terfenadine, astemizole, loratadine, clemastine, dimethindene maleate, fexofenadine hydrochloride, hydroxyzine, chlorpheniramine, azatadine maleate, methdilazine, pheniramine maleate, diphenhydramine or cetrizine; skeletal muscle relaxants such as tizanidine methocarbamol, carisoprodol, valethamate, baclofen, chlormezanone or chlorzoxazone; smooth muscle relaxants such as oxyphenonium bromide, propantheline bromide, diclomine, hyoscine buytyl bromide, mebeverine, drotaverine, clidinium bromide, isopropamide or camylofin dihydrochloride; non steroidal antiinflammatory drugs such as naproxen, mefenamic acid, nimesulide, diclofenac, tenoxicam, ibuprofen (optionally in combination with paracetamol), meloxicam, aspirin, flurbiprofen, ketoprofen, ketoprolac, phenylbutazone, oxyphenbutazone, indomethacin or piroxicam; antineoplastic agents, such as nitrogen mustard compounds (e.g. cyclophosphamide, trofosfamide, iofosfamide, melphalan or chlorambucil), aziridines (e.g. thioepa), N-nitrosurea derivatives (e.g. carmustine, lomustine or nimustine), platinum compounds (e.g. spiroplatin, cisplatin, and carboplatin), procarbazine, dacarbazine methotrexate, adriamycin, mitomycin, ansamitocin, cytosine arabinoside, arabinosyl adenine, mercaptopolylysine, vineristine, busulfan, chlorambucil, melphalan (e.g. PAM, L-PAM or phenylalanine mustard), mercaptopurine, mitotane, procarbazine hydrochloride dactinomycin (actinomycin D), daunorubicin hydrochloride, doxorubicin hydrochloride, epirubicin, plicamycin (mithramycin), mitoxantrone, bleomycin, bleomycin sulfate, aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, vindesine, paclitaxel (Taxol), methotrexate, adriamycin, arabinosyl, hydroxyurea; folic add antagonists (e.g. aminopterin, methotraxate), antagonists of purine and pyrimidine bases (e.g. mercaptopurine, tioguanine, fluorouracil or cytarabine); narcotics, opiates or sedatives such as paregoric, codeine, morphine, opium, amobarbital, amobarbital sodium, aprobarbital, butobarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam; local or general anaesthetics such as bupivacaine, chloroprocaine, etidocaine, lidocaine, mepivacaine, procaine or tetracaine, droperidol, etomidate, fentanyl citrate with droperidol, ketamine hydrochloride, methohexital sodium or thiopental; neuromuscular blockers such as atracurium mesylate, gallamine triethiodide, hexafluorenium bromide, metocurine iodide, pancuronium bromide, succinylcholine chloride, tubocurarine chloride or vecuronium bromide; or therapeutics for the hormonal system, such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate.

The term "diagnostic agent" includes within its meaning any compound, composition or particle which may be used in connection with methods for imaging an internal region of a patient and/or diagnosing the presence or absence of a disease in a patient. Diagnostic agents which may be incorporated inside the liposome or associated thereto (e.g. to its envelope, in particular to the lipophilic portion thereof) in an assembly of the invention are thus any compound, composition or particle which may allow imaging enhancement in connection with diagnostic techniques, including magnetic resonance imaging, X-ray, in particular computed tomography, optical imaging, nuclear imaging or molecular imaging. Examples of suitable diagnostic agents incorporable into or associable to a liposome are, for instance, magnetite nanoparticles; iodinated compounds, such as Iomeprol® or Iopamidol® (Bracco Imaging); hydrophilic or lipophilic paramagnetic ion chelated complexes such as, for instance, complexes of chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III); compounds comprising a hyperpolarized atom, such as $^{13}C$, $^{15}N$, $^{19}F$, $^{23}Na$, $^{31}P$ or $^{35.5}Cl$, including for instance [$^{13}C$]urea (see e.g. "Molecular imaging of endogenous substances", Golman et al. PNAS (Proceedings of the National Academy of Sciences of the USA), September 2003, vol. 100, no. 18, pp. 10435-10439) or bis-1,1-hydroxymethyl-1-$^{13}C$-cyclopropane-$D_8$ (see e.g. "Cerebral perfusion assessment by bolus tracking using hyperpolarized $^{13}C$", Johansson et al. Magnetic Resonance in Medicine, 2004, vol. 51, pp. 464-472); or radiopharmaceutical agents, such as for instance complexes of Technetium ($^{99m}Tc$), Gallium ($^{67}Ga$ or $^{68}Ga$), Indium ($^{111}In$) or Thallium ($^{201}Tl$).

For preparing the present liposome suspensions, conventional techniques known in the art can be used. Said preparation techniques typically involve dissolving the compounds forming the liposome (e.g. phospholipids) in an organic solvent, evaporating the organic solvent under vacuum to obtain a film of the liposome-forming compounds and finally hydrating said film. Typically, when the liposome-forming compound is a phospholipid, the hydration is performed at a temperature above phospholipid transition temperature. Preferably, the so obtained liposomes are subsequently calibrated at the desired size by narrowing the vesicles size distribution within appropriate limits, e.g. by extrusion through conveniently graded filtration membranes. For encapsulating a desired active compound (e.g a diagnostic or therapeutic agent) in the internal portion of the liposome, e.g. as an aqueous solution or suspension of said active compound, a preferred method involves using a solution or suspension of said active compound to hydrate the lipids at or above the lipid transition temperature, with subsequent washing (e.g. by dialysis) of the obtained liposomes, to remove the excess of non-encapsulated solution or suspension. Alternatively, the lipids are first hydrated in an unloaded aqueous carrier, and then the active compound is introduced in the interior of the liposome by transmembrane permeation loading, by incubation of the obtained liposomes in the presence of a concentrated solution of the active compound (see e.g. WO-A-92/10166 herein incorporated by reference), with subsequent washing of the liposomes.

The desired size reduction of liposomes is obtained according to conventional techniques, including sonication, extrusion or microfluidisation of the initial liposome suspension. Accordingly, hydrated liposomes obtained as above described may be exposed to ultrasonic radiations to suitably reduce the liposome dimensions. Alternatively, the hydrated liposomes can be extruded through a plurality of membranes (e.g. of polycarbonate) with decreasing pore size (e.g. 2.0, 1.0, 0.8, 0.6, 0.4, and 0.2 µm), to reduce the liposome size to the final desired dimension. As a further alternative, large vesicles can be homogenised under high pressure in a microfluidizer (e.g. from Microfluidics Corporation), to progressively reduce the liposome size to the desired size, depending on the amount of recirculation of the liposomes in the microfluidizer. These and other preparation methods are disclosed, for instance, in the reference book "Liposomes, a practical approach", edited by Roger R. C. New, Oxford University Press, 1989.

Preferably, after size reduction, about 80% of the vesicles are ±10% from any nominal value selected between 0.2 to 1.0 µm. Any other broader or narrower distribution within the foregoing limits is however admissible. After size-reduction treatment, the suspension is preferably checked to ensure that the concentration of lipids in the liposome suspension is adequate, this being optionally adjusted to be in conformity with the desired application. Adjustment can be effected by dilution with a larger volume of carrier liquid, if the lipid concentration exceeds the desired limits; on the other hand, the concentration can be increased by usual means, for instance by micro- or ultra-filtration on membranes of porosities appropriate which retain the vesicles but which are permeable to the carrier liquid.

A review of liposomes and their preparation methods can also be found in the reference book "Surfactants and Polymers in Drug Delivery", by M. Malmsten, Ch. 4, pp. 87-131, Marcel Dekker Inc. Ed., 2002.

Micelles

As know in the art, micelles are formed by amphiphilic molecules dispersed in water when the concentration of these molecules exceeds a predetermined threshold known as CMC (critical micellarization concentration). At concentrations below the CMC, the molecules are in general dispersed in the aqueous solution as single molecules. Above the CMC, the amphiphilic molecules tend to organize in supermolecular structures, in equilibrium with the free molecules in the solution, said structures being characterized by the fact that the hydrophobic (lipid) tail of the molecule is disposed towards the inner portion of the structure while the hydrophilic (polar or ionic) headgroup of the molecule is disposed on the outer portion of the structure. The CMC of an amphiphilic molecule can be determined experimentally using techniques standard in the art. For example, the CMC of a surfactant can be determined by plotting a property as a function of the concentration of the surfactant. The property usually varies linearly with the increase of surfactant concentration up to the CMC, and after this concentration, the curve (or the property) becomes non-linear. Suitable properties which can be used for the determination of the CMC include refractive index, light scattering, surface tension, electric conductivity, osmotic pressure and the like. For the purpose of the invention, preferred primary micelle-forming materials are those having a relatively low CMC, e.g. of about 10 mM or lower. Micelles have typically a dimension comprised from about 0.1 nm to about 100 nm, preferably from about 1 nm to about 50 nm. The mean diameter in number ($D_N$) is of about 50 nm or less, preferably of about 20 nm or less and much more preferably of 10 nm or less, down to e.g. 1 nm, preferably at least about 2 nm. The term "micelle" as used herein includes micellar structure formed by a mixture of two or more different compounds ("mixed micelles"), at least one of which is an amphiphilic compound capable of forming a micellar structure. The term mixed micelles thus includes within its meaning also micelles formed by at least one compound, preferably an amphiphilic compound, which is in general unable to form a micellar structure when dispersed as such in an aqueous carrier, but which is capable of forming said structure when used in combination with suitable amounts of a micelle-forming amphiphilic compound. Examples of mixed micelles are, for instance, micelles formed by unmodified phospholipids (which are in general not capable of forming micelles when dispersed as the sole material in an aqueous carrier) and by a micelle-forming compound (e.g. PEG-modified phospholipid or a fatty acid salt).

A review of micelles, micellar systems and methods of preparation thereof can be found, for instance, in the reference book: "Surfactants and Polymers in Drug Delivery", by M. Malmsten, Ch. 2, pp. 19-50, Marcel Dekker Inc. Ed., 2002). According to an aspect of the invention, a MRI responsive compound is associated to the micelle, preferably in the form of an amphiphilic compound capable of being included in the micellar structure (e.g. a complex of a paramagnetic ion with an amphiphilic chelating agent, such as a polyaminocarboxylate)

Suitable materials useful for forming micelles to be associated with a liposome in an assembly of the invention can be selected among the lipids and phospholipids material previously listed.

Examples of micelle-forming compounds are PEG-modified phospholipids, including in particular PEG-modified phosphatidylethanolamines such as DMPE-PEG, DPPE-PEG, DSPE-PEG, DAPE-PEGI; fatty acid salts, preferably alkali, in particular sodium salts, such as sodium palmitate, sodium stearate, sodium oleate, sodium linoleate, sodium dodecanoate, 1,2-dipalmitoyl-sn-3-succinylglycerate sodium salt or 1,3-dipalmitoyl-2-succinylglycerol sodium salt; sugar derivatives such as ($C_6$-$C_{10}$)alkyl-β-D-glucopyranoside, ($C_8$-$C_{12}$)alkyl-β-D-maltoside; ($C_8$-$C_{16}$)alkyldimethylammoniumpropane-sulfonate; and bile acids and derivatives thereof, such as sodium cholate or sodium deoxycholate. Polymers including hydrophobic and hydrophilic portions therein (also known as "polymeric surfactants") can also be used to prepare micellar suspensions. Examples of suitable polymeric surfactants include, without limitation, polyethyleneoxides (PEO), such as ($C_8$-$C_{16}$)n-alkyl PEO monoether, ($C_8$-$C_{10}$)n-alkyl phenyl PEO, tetramethylbutylphenyl PEO, PEO polysorbates, these PEO being sold under commercial names of Brij®, Mirj®, Lubrol®, Triton®, Nonidet® or Tween®; block copolymers such as ethyleneoxide/propyleneoxide block copolymers (e.g. Pluronic® or Synperonic®), having preferably a MW of from about 3000 to 20000 daltons, preferably of from 5000 to 15000 daltons., Advantageously, other micelle-forming compounds can be used, preferably in admixture with any of the previously listed micelle-forming compounds to form mixed micelles.

Examples of these compounds are alkylammonium salts comprising at least one ($C_{10}$-$C_{20}$), preferably ($C_{14}$-$C_{18}$), alkyl chain, such as, for instance stearylammonium chloride, hexadecylammonium chloride, dimethyidioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as 1,2-distearoyl-3-trimethylammonium-propane (DSTAP), 1,2-dipalmitoyl-3-trimethylammonium-propane (DPTAP), 1,2-dioleoyl-3-trimethylammonium-propane (DOTAP), 1,2-distearoyl-3-dimethylammonium-propane (DSDAP). Also unmodified phospholipids can be used to form micelles, such as the previously mentioned fatty acids di-esters of phosphatidylcholine, ethylphosphatidylcholine, phosphatidylglycerol, phosphatidic acid, phosphatidylethanolamine, phosphatidylserine or sphingomyelin. As these unmodified phospholipids are however in general unable to form micellar structures when dispersed in an aqueous carrier (as these compounds tend rather to associate as liposomes when dispersed in an aqueous solution), said unmodified phospholipids shall preferably amount to less than about 80%, more preferably to about 70% or less of the total weight of the mixture of compounds forming the micellar structure. According to a preferred embodiment the micellar component is formed from a mixture comprising from about 30% to 70%, preferably form about 40% to 60% by weight of unmodified phospholipids. The remainder of the mixture can be any of the above listed micelle-forming surfactants.

The overall net charge can be conferred to the micelle by any of the previously listed negatively or positively charged compounds, in particular lipids or phospholipids, including modified phospholipids.

Examples of phospholipids suitable for conferring an overall negative charge to the micelle are phosphatidylserine derivatives, such as DMPS, DPPS, DSPS; phosphatidic acid derivatives, such as DMPA, DPPA, DSPA; phosphatidylglycerol derivatives such as DMPG, DPPG and DSPG. Modified phospholipids, in particular PEG-modified phosphatidylethanolamines, can advantageously be employed to confer the desired overall negative charge to the micelle, such as, for instance DMPE-PEG750, -PEG1000, -PEG2000, -PEG-3000, -PEG4000 or -PEG5000; DPPE-PEG750, -PEG-1000, -PEG2000, PEG3000, -PEG4000 or PEG5000; DSPE-PEG750, -PEG1000, -PEG2000, PEG3000, -PEG4000 or PEG5000; DAPE-PEG750, -PEG1000, -PEG2000, PEG3000, -PEG4000 or PEG5000. Additionally, also the respective lyso-form of the above cited phospholipids, such as lysophosphatidylserine derivatives, lysophosphatidic acid derivatives (e.g. lyso-DMPA, -DPPA or -DSPA) and lysophosphatidylglycerol derivatives (e.g. lyso-DMPG, -DPPG or -DSPG). Examples of negatively charged lipids are bile acid salts such as cholic acid salts, deoxycholic acid salts or glycocholic acid salts; and fatty acid salts such as palmitic acid salt, stearic acid salt, 1,2-dipalmitoyl-sn-3-succinylglycerol salt or 1,3-dipalmitoyl-2-succinylglycerol salt. Preferably, the negatively charged compound is selected among the above cited PEG-modified phospholipids. The negatively charged component is typically associated with a corresponding positive counter-ion, which can be mono- (e.g. an alkali metal), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids suitable for conferring an overall positive charge to the micelle are esters of phosphatidylcholines, such as 1,2-Distearoyl-sn-glycero-3-Ethylphosphocholine (Ethyl-DSPC), 1,2-Dipalmitoyl-sn-glycero-3-

Ethylphosphocholine (Ethyl-DPPC). The negative counterion is preferably an halogen ion, in particular chlorine or bromine. Examples of positively charged lipids are alkylammonium salts, comprising at least one ($C_{10}$-$C_{20}$), preferably ($C_{14}$-$C_{18}$), alkyl chain, or tertiary or quaternary ammonium comprising one or preferably two ($C_{10}$-$C_{20}$), preferably ($C_{14}$-$C_{18}$), acyl chain linked to the N-atom through a ($C_3$-$C_6$) alkylene bridge, such as those previously listed.

Ethyl-DPPC, Ethyl-DSPC, DSTAP or mixtures thereof are preferably employed as positively charged compounds.

The positively charged component is typically associated with a corresponding negative counter-ion, which can be mono- (e.g. halogen), di- (e.g. sulphate) or tri-valent (e.g. phosphate). Preferably the counter-ion is selected among halogen ions, such as F− (fluorine), Cl− (chlorine) or Br− (bromine).

As above, the charged molecules can, in some embodiments, advantageously be admixed with a neutral amphiphilic compound, such as those previously listed (including neutral phospholipids), to form the desired micellar structure. Preferred neutral compounds to be admixed with the above listed charged compounds are polymeric surfactants, such as ethyleneoxide-propylenoxide block copolymers (e.g. Pluronic F68, Pluronic F108 or Pluronic F-127 from Sigma Aldrich, Missouri, USA), Polyoxyethylated alkyl ethers (e.g. Brij® 78, Sigma Aldrich), Polyoxyethylene fatty acid esters (e.g. Myrj® 53 or Myrj® 59, Sigma Aldrich); Polyoxyethylenesorbitan fatty acid esters (e.g. Tween® 60, Sigma Aldrich) or Polyethylene glycolalkylethers such as Polyethylene glycol tert-octylphenyl ether (e.g. Triton®X-100,Sigma Aldrich). According to one embodiment of the invention, the micelles are formed by mixtures of a charged amphiphilic compound with a neutral phospholipid and one or more of the above listed neutral compounds.

Preferably, the molar amount of charged surfactant forming the micelle is from about 5% to 80%, more preferably from about 10% to about 70% of the total molar amount of the micelle forming components.

According to an aspect of the invention, the mixed micelles preferably comprise a PEG-modified phospholipid, a polymeric surfactant or a mixture thereof, the presence of which allows to substantially enhance the residence time of the assembly into the blood stream. Alternatively, or in addition thereto, also bile acids, lysophospholipids or mixture thereof can be employed for enhancing the blood residence time of the assembly. The amount of compounds capable of enhancing the residence time of the assembly into the blood stream is preferably from about 10% to about 80% by mole, more preferably from about 25% to about 70% by mole of the total molar amount of micelle forming compounds.

Said enhanced residence time of an assembly according to the invention is such that, after 30 minutes from the injection, the amount of the assemblies in the blood stream is at least 50%, preferably at least 60%, of the amount of assemblies in the injected dose. Conversely, the amount of a corresponding liposome preparation in the blood stream, after 30 minutes from the injection, is typically less than 50%, in particular less than 40%, of the amount of liposomes in the injected dose. Similarly, after one hour from the injection the amount of the assemblies in the blood stream is at least 50%, and in most cases of at least 60%, of the amount of assemblies in the injected dose, while the amount of a corresponding liposome preparation in the blood stream is less than 40%, in most cases less than 30%, of the amount of liposomes in the injected dose. In particular, for liposomes having a mean diameter of about 1 μm, the amount of liposomes after one hour from injection is typically less than 10% of the amount of liposomes in the injected dose.

Active agents such as those therapeutics and diagnostics previously listed, can advantageously be associated to the micellar components, in particular those active agents comprising a suitable amphipatic structure having affinity with the micelle-forming compounds or those which may be encapsulated in the micellar component. An active agent may represent from about 10% to about 80% of the total weight of the micelle, preferably from about 25% to about 70%.

Preferably, an image enhancing agent is associated to the micellar compound, in particular an MRI responsive compound. The MRI responsive compound associated to the micelle is preferably in the form of an amphiphilic compound capable of being included in the micellar structure, e.g. by hydrophobic interactions of the lipophilic portion of said compound with the lipophilic portions of the micelle-forming components.

According to a preferred embodiment, the MRI-responsive amphiphilic compound is a paramagnetic metal ion complexed by chelating molecule including a lipophilic moiety, hereinafter referred to as a chelated paramagnetic ion. Preferred paramagnetic metal ions have atomic numbers 21-29, 42, 44, or 57-83. This includes ions of the transition metal or lanthanide series which have at least one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III). Additionally, heteromultimers of the present invention may also be conjugated with one or more superparamagnetic particles.

One skilled in the art will select a metal according to the dose required to detect target containing tissue and considering other factors such as toxicity of the metal to the subject. Generally, the desired dose for an individual metal will be proportional to its relaxivity, modified by the biodistribution, pharmacokinetics and metabolism of the metal. The trivalent cation, $Gd^{3+}$ is particularly preferred for MRI contrast agents, due to its high relaxivity and low toxicity, with the further advantage that it exists in only one biologically accessible oxidation state, which minimizes undesired metabolization of the metal by a patient. Another useful metal is $Cr^{3+}$, which is relatively inexpensive. The chelating molecule is preferably an amphipatic chelating agent. In particular, said molecule preferably comprises a chelating hydrophilic portion, including one or more polar groups (that act as a ligand for, and complex with, a paramagnetic metal) and a lipophilic portion capable of interacting with lipophilic portions of the other micelle-forming compounds, to integrate the complex into the micellar structure. The chelating portion is preferably a residue of a chelating acid commonly employed in the art, more preferably of a chelating polycarboxylic or polyaminocarboxylic acid. Suitable chelators known in the art include acids with methylene phosphonic acid groups, methylene carbohydroxamine acid groups, carboxyethylidene groups, or carboxymethylene groups. Examples of chelators include, but are not limited to, diethylenetriamine pentaacetic acid (DTPA), 1,4,7,10-tetraazacyclododecane-1,4,7,10-tetraacetic acid (DOTA), 1,4,7,-tricarboxymethyl 1,4,7,10teraazacyclododecane triacetic acid (DO3A), ethylenediaminetetraacetic acid (EDTA), and 1,4,8,11-tetraazacyclotetradecane-1,4,8,11-tetraacetic acid (TETA).

Additional chelating ligands are ethylenebis-(2-hydroxyphenylglycine) (EHPG), and derivatives thereof, including 5-α-EHPG, SBr-EHPG, 5-Me-EHPG, 5t-Bu-EHPG, and Ssec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2(hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g. benzo-DOTA, dibenzo-DOTA, benzo-NOTA, where NOTA is 1,4,7-triazacydononane N,N',N''-triacetic acid, benzo-TETA, benzo-DOTMA, where DOTMA is 1,4,7,10-tetraazacyclododecane-1,4,7,10-tetra(methyl tetraacetic acid), or benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N''-tris(2,3-dihydroxybenzoyl)-tricatecholate (LICAM); derivatives of 1,3,5-N,N',N''-tris(2,3-dihydroxybenzoyl) aminomethylbenzene (MECAM); or derivatives DO3A, such as HP-DO3A (1,4,7,10-tetraazacyclo-dodecan-1-(2-hydroxypropyl)-4,7,10-triacetic acid). Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, each of which is hereby incorporated by reference in its entirety. Preferred chelators for use in the present invention are DO3A, HP-DO3A, DTPA or DOTA. Use of the chelating moieties DO3A or HP-DO3A is particularly preferred.

The lipophilic moiety can be linked to the respective chelating portion (e.g. any of the above illustrated chelators) of the chelating molecule according to known techniques. For instance, a hydrophobic moiety can be linked to a carboxylic acid residue through an ester bond or an amide bond. Examples of suitable lipophilic moieties linkable through an ester bond to the chelating moiety include residues of ($C_1$-$C_{24}$) alcohols, preferably ($C_8$-$C_{24}$), more preferably ($C_{10}$-$C_{20}$) linear aliphatic alcohols, such as, for instance, n-decyl alcohol, lauryl alcohol, myristyl alcohol, cetyl alcohol, or n-octadecyl alcohol; aromatic alcohols, such as, for instance benzyl alcohol, mono-, di- or tri-($C_1$-$C_4$)alkyl-phenyl alcohols; and mixtures thereof. Similarly, preferred amines to be linked through an amido bond to the carboxylic moiety of a chelating acid include ($C_1$-$C_{24}$)alkyl, preferably ($C_8$-$C_{24}$) alkyl, more preferably ($C_{10}$-$C_{20}$)alkyl linear aliphatic amines, such as, for instance, n-decyl amine, n-dodecyl amine, n-tetradecyl amine, n-hexadecyl amine or n-octadecyl amine; aromatic amines, such as, for instance benzyl amine, mono-, di- or tri-($C_1$-$C_4$)alkyl-phenyl amine; and mixtures thereof.

Examples and preparation of preferred amphipatic chelates and complexes thereof with paramagnetic metals are disclosed, for instance, in U.S. Pat. Nos. 6,342,598 or 6,652,834, both herein incorporated by reference.

Alternatively, a nitrogen atom of any of the previously listed polyaminocarboylic acids can be provided with a ($C_8$-$C_{24}$), more preferably ($C_{10}$-$C_{20}$), linear alkyl or hydroxy alkyl moiety, as described in the above cited U.S. Pat. No. 6,342,598.

Alternatively, a polycarboxylic chelating agent can be provided with lipophilic hydrophobic groups linked to the alkylene segments of the molecular back-bone, or to the alpha-carbon of the carboxylate functions or to a hydroxyl group when present in the chelating agent, as described in U.S. Pat. No. 6,652,834.

Particularly preferred are those derivatives of 1,4,7,-tricarboxymethyl1,4,7,10 teraazacyclododecane triacetic acid (DO3A) bearing on the N-10 position a suitable lipophilic moiety, such as [10-[2-(dioctadecylamino)-2-oxoethyl]-1,4,7,10-tetraazacyclododecane-1,4,7-triacetic acid, which forms the corresponding [10-[2-(dioctadecylamino)-2-oxoethyl]-1,4,7,10-tetraazacyclododecane-1,4,7-triacetate(3-)] Gadolinium complex.

Preparations of chelated paramagnetic metal ion can be made according to known procedures, such as for instance the preparation disclosed by G. W. Kabalka et al., Magnetic Resonance in Medicine 8 (1988), 89-95.

According to an alternative embodiment the MRI responsive agent can be a magnetite nanoparticle. Magnetite nanoparticles can be, for instance, admixed with a negatively charged amphiphilic material (and optionally a neutral one), such as those previously mentioned, in order to stabilize said particles and keep them dispersed in an aqueous solution in micellar form. U.S. Pat. No. 5,545,395, herein incorporated by reference, gives some examples of preparation of said stabilized magnetite particles, e.g. by using a mixture of DPPA and Pluronic® for stabilizing said particles.

Further to those indicated above, any other MRI responsive agent stably associable to the micellar structure can be used. For instance, any amphiphilic compound comprising a hyperpolarized atom such as those previously mentioned, preferably $^{13}C$, can be suitably incorporated into a micelle associated to a liposome in an assembly according to the invention. The molar amount of the MRI responsive agent in the micellar component, in particular of the paramagnetic metal ion, shall be sufficiently high to allow the desired diagnostic image enhancement. Preferably, the molar amount of MRI responsive agent is preferably of at least 25% of the total molar of the micelle-forming material, more preferably of at least 50% and much more preferably of at least 70%. Typically, amounts higher than about 99% are in general not desirable, as this would excessively lower the amount of charged component in the micelle. More preferably, the molar amount of MRI responsive agent is not higher than about 95%.

Targeting Ligand

Advantageously, the micelles of an assembly according to the invention can further include a compound having a targeting activity, i.e. a targeting ligand, allowing the assembly to bind to a specific target.

The targeting ligand included in the micelle may be synthetic, semi-synthetic, or naturally-occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, therapeutic agents and genetic material, including nucleosides, nucleotides and polynucleotides.

The term "target" or "target molecule" refers to any substance that a targeting ligand can bind to, such as proteins or polypeptides, cells, receptors, carbohydrates, lipids, etc.

Examples of suitable targets and targeting ligands are disclosed, for instance, in U.S. Pat. No. 6,139,819, which is herein incorporated by reference.

The targeting ligand can be an amphiphilic compound per se which is admixed with the other components of the micelle composition or can be a compound which is bound to an amphiphilic molecule employed for the formation of the micelle.

In one preferred embodiment, the targeting ligand can be bound to an amphiphilic molecule of the micelle through a covalent bond. In such a case, the specific reactive moiety that needs to be present on the amphiphilic molecule will depend on the particular targeting ligand to be coupled thereto. As an example, if the targeting ligand can be linked to the amphiphilic molecule through an amino group, suitable reactive moieties for the amphiphilic molecule may be isothiocyanate groups (that will form a thiourea bond), carboxylic acids or reactive esters (to form an amide bond), aldehyde groups (for the formation of an imine bond to be reduced to an alkylamine bond), etc.; if the targeting ligand can be linked to the amphiphilic molecule through a thiol group, suitable complementary reactive moieties for the amphiphilic molecule include haloacetyl derivatives or maleimides (to form a thioether bond); and if the targeting ligand can be linked to the amphiphilic molecule through a carboxylic group, suitable reactive moieties for the amphiphilic molecule might be amines and hydrazides (to form amide or alkylamide bonds). In order to covalently bind a desired targeting ligand, at least part of the amphiphilic compound forming the micelle shall thus contain a suitable reactive moiety and the targeting ligand containing the complementary functionality will be linked thereto according to known techniques, e.g. by adding it to an aqueous dispersion comprising the amphiphilic components of the micelle. The amphiphilic compound can be combined with the desired targeting ligand before preparing the micelle, and the so obtained combination can be used in the preparation process of the micelle. Alternatively, the targeting ligand can be linked to the respective amphiphilic compound during the preparation process of the micelle or can be directly linked to the amphiphilic compound already included in a micellar structure.

According to an alternative embodiment, the targeting ligand may also be suitably associated to the micelle via physical and/or electrostatic interaction. As an example, a functional moiety having a high affinity and selectivity for a complementary moiety can be introduced into the amphiphilic molecule, while the complementary moiety will be linked to the targeting ligand. For instance, an avidin (or streptavidin) moiety (having high affinity for biotin) can be covalently linked to a phospholipid while the complementary biotin moiety can be incorporated into a suitable targeting ligand, e.g. a peptide or an antibody. The biotin-labelled targeting ligand will thus be associated to the avidin-labelled phospholipid of the micelle by means of the avidin-biotin coupling system. Alternatively, both the phospholipid and the targeting ligand can be provided with a biotin moiety and subsequently coupled to each other by means of avidin (which is a bifunctional component capable of bridging the two biotin moieties). Examples of biotin/avidin coupling of phospholipids and peptides are also disclosed in the above cited U.S. Pat. No. 6,139,819. Alternatively, van der Waal's interactions, electrostatic interactions and other association processes may associate or bind the targeting ligand to the amphiphilic molecules.

According to an alternative embodiment, the targeting ligand can be a compound which is admixed with the components forming the micelle such as, for instance, a lipopeptide as disclosed e.g. in International patent Applications WO 98/18501 or 99/55383, both herein incorporated by reference. Alternatively, a micelle can first be manufactured, which comprises a compound having a suitable moiety capable of interacting with a corresponding complementary moiety of a targeting ligand; thereafter, the desired targeting ligand is added to the micelle suspension, to bind to the corresponding complementary moiety on the micelle. As an additional alternative, an assembly can be prepared, which comprises a micelle including a compound having a suitable moiety capable of interacting with a corresponding complementary moiety of a targeting ligand; thereafter, the desired targeting ligand is added to the assembly suspension, to bind to the corresponding moiety on the micelle. Examples of suitable specific targets to which the assembly can be directed are, for instance, fibrin and the GPIIbIIIa binding receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544, which is herein incorporated by reference. Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005 and WO 03/084574, both herein incorporated by reference.

Mixed micelles containing the desired amphiphilic components, the chelated paramagnetic metal ion and, optionally, a targeting agent, can be prepared as known in the art, e.g. according to the preparation method disclosed in European patent EP 804 251, herein incorporated by reference.

For instance, the components can be dispersed in an aqueous liquid carrier under agitation. Examples of suitable liquid carriers are water, saline solution (sodium chloride 0.9%), Phosphate buffered saline (10 mM, pH 7.4), HEPES buffer (20 mM, pH 7.4), Glucose 5% w/w in water. For instance, the above compounds can be dispersed in a concentration of from about 1 to 100 mg/ml in an aqueous liquid and dissolved by means of gentle mechanical agitation or sonication.

The micelles can then be stored as an aqueous dispersion (e.g. in the aqueous carrier used for their preparation) before being admixed with a suspension containing liposomes. Alternatively, the micelle suspension can be freeze-dried according to conventional techniques, to eliminate the liquid and store the final dry product for the subsequent uses.

Assembly

The preparation of an assembly according to the invention can be obtained according to conventional methods, e.g. by admixing an aqueous suspension comprising the liposomes (obtained according to any of the above cited manufacturing methods) with an aqueous suspension comprising micelles obtained as above described.

Optionally, the so obtained mixture can be subjected to one or more washing steps, in order to remove the excess of non-associated components. For the purposes of the present invention, the term "washing step" includes within its meaning any method or process directed to separate and/or at least partially remove the excess of non-associated materials, components, particles and the like from a suspension of a desired compound. Suitable separation methods include, for instance, dialysis, decantation, centrifugation, ultrafiltration or microfiltration, centrifugation being generally preferred. Suitable conventional washing solutions can be employed in the washing step, such as distilled water, phosphate buffered saline, Tris/glycerol buffer, saline or 5% glucose solution. The phase of the washed mixture comprising the assembly of the invention is thus separated and collected; optionally, the recovered assembly-containing suspension is finally diluted before use, e.g. with any of the above cited physiologically acceptable carrier.

The suspension comprising the assembly of the invention can be stored for a subsequent administration or can be directly administered to a patient. If desired, the liquid carrier of the suspension can be eliminated (e.g. by freeze-drying) to obtain a dry powder of the assembly which can be stored for relatively long periods of time before reconstitution.

Alternatively, the two components of the assembly can be stored as separate compositions in dried form (e.g. freeze dried) and reconstituted as a suspension before administration. The reconstitution with an aqueous liquid carrier may take place separately on the two dried compositions comprising the respective components of the assembly, thus obtaining two separate suspensions which are subsequently admixed to obtain the desired assembly suspension. Alternatively, the two dried compositions may be admixed together and then reconstituted as a single suspension with an aqueous liquid carrier. According to a preferred embodiment, the dried micellar composition is first reconstituted with a physiologically acceptable aqueous carrier and the obtained suspension is then used for reconstituting the dried liposome composition, to finally obtain a suspension of the assembly.

For the preparation of the assembly it may be advantageous to add an excess amount of micelles with respect to the amount of micelles which is desired to have in the final assembly, in particular because a certain amount of said micelles can be removed during the optional washing steps of the assemblies' suspension. The excess of micelles is for convenience expressed as the excess of negative (or positive) charges in the micellar preparation with respect to the amount of positive (or negative) charges in the liposomal suspension, the charges being indicated as "equivalent of charges". The term "equivalent of charge" (EC) refers to the number of charges per mole of a compound; thus, one mole of a mono-ionic compound contains one EC, one mole of a di-ionic compound contains two EC and so on. In general, it is preferred that the amount of EC in the micellar composition is substantially equal to the EC in the composition of the liposomes (i.e. EC ratio of about 1:1). The ratio between EC in the micelle preparation with respect to the EC in the liposome preparation can thus vary, for instance, from about 1:2 to about 3:1, preferably from 2:3 to 3:2. In order have a practical indication of the effectiveness of the assembly, the Applicant has found useful to refer to the $\zeta$-potential (zeta-potential) of the liposome suspension and of the assembly suspension. The $\zeta$-potential, also called electrokinetic potential, is the electric potential at the surface of a colloidal particle relative to. the potential in the bulk medium at a long distance. It can be measured according to conventional micro-electrophoresis analytical methods, e.g. via the determination of the velocity of the particles in a driving electric field by Laser-Doppler-Anemometry. For example, the ZetaSizer 3000 Has (Malvern Instrument GmbH) can be advantageously used. In the practice, the $\zeta$-potential of the initial suspension of liposomes is first determined, which can have a positive or negative value, depending whether the liposomes contain positively or negatively charged compounds, respectively. Then, the $\zeta$-potential is measured on the final suspension containing the assembly (i.e. after the necessary washing steps for removing possibly unbound micelles). In general, the addition of micelles of opposite sign with respect to the liposomes determines a more or less pronounced decrease in absolute value of the $\zeta$-potential of the suspension. In particular, suspensions comprising positively charged liposomes will show a decrease of the $\zeta$-potential upon addition of a suspension of negatively charged micelles, while suspensions comprising negatively charged liposomes will show a relative increase of the $\zeta$-potential (i.e. a decrease in absolute value) upon addition of a suspension of positively charged micelles. As observed by the Applicant, preferred assemblies are those suspensions showing a substantial decrease in absolute value with respect to the $\zeta$-potential of the initial liposome suspension, i.e. a decrease of at least 50%, preferably of at least 75% and more preferably of at least 90% of said initial value. Particularly preferred assemblies' suspensions are those showing a substantially neutral $\zeta$-potential (i.e. 0±15 mV, corresponding to an absolute decrease of about 100% with respect to the initial potential of the liposomes suspension) or a $\zeta$-potential opposite in sign with respect to the $\zeta$-potential of the initial liposomal suspension. As observed by the Applicant, when the $\zeta$-potential of the assembly suspension remains equal in sign with an absolute decrease of less than 50% with respect to the $\zeta$-potential of the initial liposome suspensions, this may be an indication that an insufficient number of micelles are associated to the liposomes.

According to a preferred embodiment, the amount of charged micelles in the assembly is such as to confer a substantially neutral $\zeta$-potential to said assembly or a $\zeta$-potential which is opposite in sign with respect to the $\zeta$-potential of the liposome suspension. As observed by the Applicant, to obtain said neutral or opposite in sign $\zeta$-potential of the assembly it is however not necessary that the assembly contains an excess of equivalents of charge from the micelles. As a matter of fact, it has been observed that assemblies composed of positive liposomes and negative micelles and having a ratio between EC in the micelles and equivalents of opposite charge in the liposomes of about 1:5 (i.e. an excess of about 5 times of positive charges on the liposomes) may nevertheless show a substantially neutral or negative $\zeta$-potential. Although not wishing to be bound to any particular theory, it may be supposed that the (negative) charges comprised in the micelles are disposed on the outer surface of the assembly; if the number of micelles associated to the liposome is sufficiently high, the excess of (positive) opposite charges on the liposome may result, at least partially, screened by said micelles. Thus, as the $\zeta$-potential measured on a particle is strongly influenced by the charges present on the outer boundary of said particle, even an assembly having an excess of (positive) equivalents of charge deriving from a liposome may show a negative $\zeta$-potential, if the amount of (negatively) charged micelles is sufficient to partially screen the (positive) charges of the liposome. All the above is of course also applicable to assemblies formed by negatively charged liposome and positively charged micelles.

Injectable compositions after reconstitution of the lyophilised contrast agent should be, as far as possible, isotonic with blood. Hence, before injection, small amounts of isotonic agents may also be added to the suspensions comprising the assembly of the invention. The isotonic agents are physiological solutions commonly used in medicine such as, for example, aqueous saline solution (0.9% NaCl), 2.6% glycerol solution or 5% dextrose solution. The reconstitution of the aqueous suspensions is generally obtained by simple dissolution of the dried components and gentle agitation.

The volume and concentrations of the reconstitution liquid may desirably be balanced to make the resulting ready-to-use formulations substantially isotonic. Hence the volume and concentration of reconstitution fluid chosen will be dependent on the type and amount of stabilizer (and other bulking agents) present in the freeze-dried product.

The assembly of the invention can be included into diagnostic kits comprising the assembly of the invention or its respective separate components, optionally further comprising the aqueous liquid carrier.

According to a first embodiment, said kit is a two component kit comprising the assembly of the invention together with an aqueous liquid carrier. Said two component kit can include two separate containers or a dual-chamber container.

In the former case the first container is preferably a conventional septum-sealed vial, wherein the vial containing the assembly as a lyophilized residue (obtained according to any of the above illustrated methods) is sealed with a septum through which the carrier liquid may be injected for reconstituting the suspension of assemblies. The carrier liquid is contained into a second container which preferably takes the form of a syringe. The syringe is preferably pre-filled with the reconstituted suspension and used subsequently to administer the contrast agent by injection. Instead of the formed assembly, the first container can alternatively contain mixtures of separately freeze-dried micelles and liposomes compositions, which will form the desired assembly upon reconstitution with the aqueous carrier. Although in general hand shaking of the container provides the desired energy for reconstituting the suspension, means for directing or permitting application of sufficient energy towards the container can be provided (e.g. a Vortex mixer), in order to assure suitable reconstitution of the assemblies' suspension. The dual-chamber container is preferably a dual-chamber syringe, where the components are kept separated e.g. by means of a removable septum, and once the lyophilisate has been reconstituted by gentle shaking, the container can be used directly for injecting the contrast agent. As before, means for directing or permitting application of sufficient energy towards of the container can be provided.

It can be appreciated by one ordinary skilled in the art that other two-chamber reconstitution systems capable of combining the dried powder with the aqueous solution in a sterile manner are also within the scope of the present invention. According to an alternative embodiment, a kit according to the invention is an at least two component kit comprising a micelle composition, a liposome composition and, optionally, an aqueous carrier. The kit is preferably presented as at least two separate containers, the first one containing the lyophilized liposome composition and the second one containing the desired lyophilized micelle composition (e.g. where the micelles comprise a suitable targeting ligand). A third optional container, containing the aqueous carrier for reconstitution can advantageously be included in the kit. If desired, additional containers containing further lyophilized micelles (e.g. comprising a second targeting ligand) or liposomes compositions can be included in the kit. For administration, the micellar suspension is first reconstituted in the aqueous carrier and the obtained suspension is then used for reconstituting the liposome composition, thus forming the desired assembly suspension.

No specific containers vial or connection systems are required; the present invention may use conventional containers, vials and adapters. The only requirement is a good seal between the stopper and the container. The quality of the seal, therefore, becomes a matter of primary concern; any degradation of seal integrity could allow undesirable substances to enter the vial. In addition to assuring sterility, vacuum retention is essential for products stoppered at ambient or reduced pressures to assure safe and proper reconstitution. The material of the stopper forming the gas-seal of the container is preferably an elastomeric compound or multicomponent formulation based on an elastomer, such as poly(isobutylene) or butyl rubber. Conveniently a butyl rubber stopper from Daiko Seiko ltd. can be used.

The composition of the invention may be used in the same manner as conventional therapeutic or diagnostic compositions. For instance, when the composition comprises a MRI responsive agent, certain MR techniques and pulse sequences may be preferred when imaging a target-containing tissue such as, for example, a site of angiogenesis, to enhance the contrast of the site to the background blood and tissues. These techniques include (but are not limited to), for example, black blood angiography sequences that seek to make blood dark, such as fast spin echo sequences (see e.g. Alexander et al., Magnetic Resonance in Medicine, 40(2): 298-310 (1998)) and flow-spoiled gradient echo sequences (see e.g. Edelman et al., Radiology, 177(1): 45-50 (1990)). These methods also include flow independent techniques that enhance the difference in contrast, such as inversion-recovery prepared or saturation-recovery prepared sequences that will increase the contrast between target containing tissue, such as an angiogenic tumor, and background tissues. Finally, magnetization transfer preparations may also improve contrast with these agents (see e.g. Goodrich et al., Investigative Radiology, 31(6): 323-32 (1996)). The assembly of the invention is preferably administered to the patient in the form of an injectable composition. The method of administering is preferably parenterally, meaning intravenously, intraarterially, intrathecally, interstitially, intradermally or intracavitarilly. For imaging active angiogenesis, intravenous or intraarterial administration is preferred.

When the assembly contains a MRI responsive compound and a targeting ligand, it is contemplated that the subject will receive a dosage of contrast agent sufficient to enhance the MR signal at the target (e.g. a site of angiogenesis) at least 10%. After injection of the assembly including the MRI reagent, the patient is scanned in the MRI machine to determine the location of any sites containing the target. In therapeutic settings, upon target localization, a therapeutic agent can be immediately administered, if necessary, and the patient can be subsequently scanned to visualize the therapeutic effect.

The following examples are provided to illustrate the invention more in detail.

EXAMPLES

The following materials are employed in the examples:

| | |
|---|---|
| SPC3 | Hydrogenated derivative of natural soy phosphocholine (Lipoid): Mean composition: 4:1 (w/w) Distearoyl-phosphatidylcholine (DSPC) and Dipalmitoylphosphatidylcholine (DPPC) |
| Ethyl-SPC3 | Ethyl derivative of SPC3 (prepared according to the procedure described by R. C. McDonald et al., Journal of Pharmaceutical sciences, vol. 88, no. 9, pp. 896—900, Sept. 1999)) |
| DSPE-PEG2000 | Distearoylphosphatidylethanolamine modified with PEG2000, sodium salt (Genzyme) |
| Biotinated DPPE-PEG2000 | DSPE-PEG2000 with biotinated cap terminal (Avanti Polar Lipids) |
| DSPG•Na | Distearoylphosphatidylglycerol sodium salt (Genzyme) IUPAC: 1,2-Dipalmitoyl-sn-glycero-3-[phospho-rac-(1-glycerol)] |
| Pluronic F108 | Ethyleneoxide/propyleneoxide block copolymer (Fluka) |

-continued

| | |
|---|---|
| Gd-complex | ([10-[2-(dioctadecylamino)-2-oxoethyl]-1,4,7,10-tetraazacyclododecane-1,4,7-triacetate(3-)]Gadolinium complex, prepared according to example 5 of U.S. Pat. No. 6,652,834 |
| $^{14}$C-tripalmitin | $^{14}$C radioactive labelled tripalmitin (Amersham) |
| Tween 20 | Polyoxyethylene 20 sorbytane monolauretate (Sigma) |
| PBS | Phosphate buffered saline: 10 mM sodium phosphate, NaCl 0.9% w/w, pH = 7.4 |

ζ-potentials of liposome and assembly suspensions are determined by using a Malvern Zetasizer 3000Hsa in glucose 0.4 M.

Example 1

Preparation of Positively Charged Liposomes 1.0 μm Diameter 1037.7 mg (1.332 mmol) of SPC3, 74.9 mg (0.089 mmol) of Ethyl-SPC3, and 137.4 mg (0.355 mmol) of cholesterol (Fluka) are dissolved in a mixture of 17 ml of methanol and 33 ml of chloroform. The solution is filtered on a 0.2 μm sterile filter (Macherey Nagel) and a tracer quantity of 14C-tripalmitin (10 μl in CHCl3; specific activity 50 μCi/ml) is added as marker. The organic solvents are removed by evaporation in a rotary evaporator (Rotavapor) at 40° C. under reduced pressure and the residue is dried overnight at the same temperature under a pressure of 1 Torr.

50 ml of a Iomeprol solution (Bracco Imaging), corresponding to 280 mg of iodine per ml, are added to the dry lipids, so that the obtained solution contains approximately 25.3 mg of lipids/mi (CLip). The solution is then heated for about half an hour at 80° C. under gentle stirring to effect hydration of the lipids with subsequent liposome vesicles formation. The liposome suspension is then extruded in succession for five times through a 2.0 μm pore size polycarbonate filter (Nucleopore™).

In order to determine the amount of iodine effectively encapsulated in the liposome vesicles, a 1 ml aliquot of the filtered preparation is dialyzed (dialysis bag from Serva; Mw cutoff≈10.000-15.000) for about 10-12 hrs against 1 l of PBS buffer. The dialysis operation is repeated once to ensure that all free, non-encapsulated iodine has been removed. A 10% sodium dodecyl sulfate solution (0.1 ml) is added to the dialyzed solution (0.9 ml) and the mixture is heated at 40° C. for 5 minutes to destroy liposomes and free the entrapped iodine. The content of iodine in the final preparation is determined by measuring the optical density of this solution at 260 nm. In the specific, the final preparation contained 230 mg/ml of Iomeprol (corresponding to 113 mg of liposome-entrapped iodine per ml of suspension).

The amount of lipids effectively present in the preparation is determined by measuring the radioactivity of the sample using a liquid scintillation analyzer (Packard 2200-CA, TRI-CARB®). In the specific, a lipid concentration (CLip) of 25 mg/ml was determined.

The whole volume of filtered liposome suspension is subjected to dialysis (dialysis bag from Serva; Mw cut-off≈10.000-15.000, PBS) to remove the free non-encapsulated iodine from the suspension and then concentrated by ultrafiltration (Amicon cell membrane) to increase about two times the lipid concentration (about 30 mg/ml).

The mean size of the liposome vesicles and the vesicle size distribution are determined by a Dynamic Light Scattering method (DLS) (also known as "Photon Correlation Spectroscopy—PCS) by using a Malvern MasterSizer MS20 (Malvern Instruments). The specific determination indicated that the mean size of the vesicles in the present preparation was of about 1.05 μm.

Example 1a

The same procedure of Example 1 is applied, but the dried lipids obtained after evaporation of the organic solvent are hydrated with 50 ml of a 0.4 M glucose solution (instead of the 50 ml of Iomeprol® solution). After extrusion as in example 1, liposomes with a mean diameter of about 1 μm are obtained.

Example 2

Preparation of Positively Charged Liposomes 0.4 μm Diameter

The same procedure of example 1 is followed, with the additional step that after the five-times extrusion through the 2.0 μm polycarbonate filter, the liposome suspension is further filtered for five times through a 1.0 μm pore size polycarbonate filter and for further five times through a 0.6 μm pore size polycarbonate filter.

Encapsulated iodine: 67.7 mg/ml; liposome mean diameter: 0.42 μm.

Example 3

Preparation of Positively Charged Liposomes 0.2 μm Diameter

The same procedure of example 2 is followed, with the additional step that after the five-times extrusion through the 0.6 μm polycarbonate filter, the liposome suspension is further filtered for five times through a 0.4 μm polycarbonate filter and for five times through a 0.2 μm polycarbonate filter.

Encapsulated iodine: 33.6 mg/ml; liposome mean diameter: 0.22 μm.

All liposomal preparations of examples 1-3 show a ζ-potential of about +45 mV±2.

Example 4

Preparation of Negatively Charged Micelles with Gd-complex 200 mg of Gd-complex and 200 mg of DSPE-PEG2000 are dissolved in 10 ml of distilled water and the mixture is homogenised by sonication for about 30 min at 70° C. (Branson Sonifier, output 40).

Proton spin relaxivities of the micelle suspension are measured using a Minispec PC-120 (Bruker) apparatus, operating under 0.47 Tesla (20 MHz). EDM 510A (EDM=Experiment Definition Module) is used to measure the spin-lattice relaxation time T1 by the "inversion recovery" method. EDM 610A was used to measure the spin-spin relaxation time T2 by the Carr-Purcell-Meiboom-Gill (GPMG) technique. The longitudinal ($r_1$) and transversal ($r_2$) relaxivities (expressed in $s^{-1}mM^{-1}=1/T$) measures on a 1 mM suspension prepared as above were as follows:

($r_1$)=22.6; ($r_2$)=26.3

Example 5

Preparation of Assembly with Positively Charged Liposomes and Negatively Charged Micelles with Gd-complex Three assembly preparations are carried out, by admixing 4 ml of a micelle suspension prepared according to example 4 with 16 ml of each of the three liposome suspension prepared according to examples 1 to 3, in order to obtain respective assemblies suspensions A1, A2, and A3. The mixture is gently stirred for 4 hours and then left overnight at 4° C. Afterwards, the suspension is brought at room temperature and centrifuged for one hour at 30,000 g (Heraeus Supratech 22). Liposome-micelle assemblies are then recovered from the pellet of the centrifuged suspension (discarding the supernatant) and suspended in 0.4 M glucose, to a total volume of 16 ml and gently stirred overnight.

For each preparation, the iodine content and the T1 and T2 relaxation times are determined as illustrated in examples 1 and 4, respectively, by admixing 0.4 ml of each preparation with 3 ml of blood (rat). Relaxivities r1 and r2 are then calculated from respective T1 and T2 values. Relaxivities values r1 and r2 (in $s^{-1}mM^{-1}$) measured on the assemblies preparations A1, A2 and A3 were as follows:

A1: r1=21.1, r2=25.2;
A2: r1=19.6, r2=23.5;
A3: r1=22.7, r2=25.6.

For the three assembly preparations, the measured ζ-potential was of about +5 mV±1.

Example 5a

The same procedure of example 5 is followed, but the 4 ml of micelle suspension of example 4 are admixed with 16 ml of a liposome suspension of example 1a. The mixture is gently stirred for 4 hours and then left overnight at 4° C. Afterwards, the suspension is brought at room temperature and the formed assemblies are separated from the excess of unbound micelles by means of size exclusion chromatography, eluting with a 0.4 M glucose solution.

Example 6

Preparation of Assembly with Negatively Charged Liposomes and Positively Charged Micelles with Gd-complex A suspension of negatively charged liposomes comprising 840.5 mg (1.079 mmoles) of SPC3, 58.1 mg (0.073 mmoles) of DSPG·Na and 113.7 mg (0.294 mmoles) of cholesterol dissolved in 20 ml of Iomeprol solution is prepared according to the procedure outlined in example 1. Vesicles' mean size was of about 0.95 μm.

A suspension of positively charged micelles comprising 200 mg of Gd-complex, 300 mg of Pluronic F108 and 61.6 mg of Ethyl-SPC3 dissolved in 20 ml of distilled water is prepared according to the procedure outlined in example 4. Micelles' mean size was of about 0.80 nm.

1 ml of the liposomes suspension is admixed with 1 ml of the micelles suspension according to the procedure of example 5. The resulting recovered assembly showed the following relaxivities values: r1=21.6 $s^{-1}mM^{-1}$, r2=24.2 $s^{-1}mM^{-1}$.

The ζ-potential measured on the initial liposomal preparation is of about 32 mV, while the ζ-potential of the final assembly preparation is of about −3 mV.

Example 7

Preparation of Assembly with Positively Charged Liposomes and Negatively Charged Micelles with Magnetite Particles A suspension of positively charged liposomes is prepared according to the procedure outlined in example 1.

Magnetite partides coated with DPPA/Pluronic F108 (FE/DPPA/Pluronic F108 ratio 3/15/15 in mg/ml) are prepared according to U.S. Pat. No. 5,545,395. The solution is diluted with 10 ml of 5% glucose.

5 ml of liposome suspension are admixed with 4.5 ml of micellar magnetite suspension, kept for 3 hours under rotating agitation, then centrifuged at 3500 g for 30 minutes. The supernatant is discarded and the micelle-containing solution is diluted with 50 ml of 5% glucose. Relaxivity value r2 measured on the obtained assembly suspension was of 366.6 $s^{-1}mM^{-1}$.

Example 8

Preparation of Assembly with Positively Charged Liposomes Containing Gd-complex and Negatively Charged Micelles with Gd-complex 1156.5 mg of SPC3, 163.5 mg of cholesterol, 178.5 mg of Ethyl-SPC3 and 375.0 mg of Gd-complex are dissolved in 100 ml of $CHCl_3$ The solvent is evaporated on rotating evaporator at 50° C. and the residue is dried overnight in a vacuum oven. The dried lipid film is rehydrated by adding 150 ml of Iomeprol (280 mg Iode/ml) during 45 min at 65° C. under slight agitation. The obtained liposome suspension is then passed five times through a 2 μm polycarbonate filter (Nucleopore) and finally dialysed against glucose 0.4 M, to remove the non-entrapped Iomeprol.

Relaxivities values determined on the liposomes were as follows:

r1 9.3 $s^{-1}mM^{-1}$
r2 12.6 $s^{-1}mM^{-1}$ 5 ml of a micellar suspension containing 26.02 mg/ml of Gd-complex and 20.04 mg/ml of PE-PEG 2000 in water are added to 20 ml of the above liposome suspension. The mixture is left at room temperature for about three hours and then centrifuged at 35,000 g for 45 minutes. The supernatant is discarded and the recovered assemblies are resuspended in glucose 0.4 M.

Relaxivities values measured on the assembly's suspension were as follows:

r1 16.9 $s^{-1}mM^{-1}$
r2 21.6 $s^{-1}mM^{-1}$

Example 9

Evaluation of Blood Circulation of Assembly Preparations

The assembly preparations obtained according to example 5 are evaluated for their respective blood circulation properties and compared with corresponding liposome preparations obtained according to examples 1 to 3.

Figure 2:
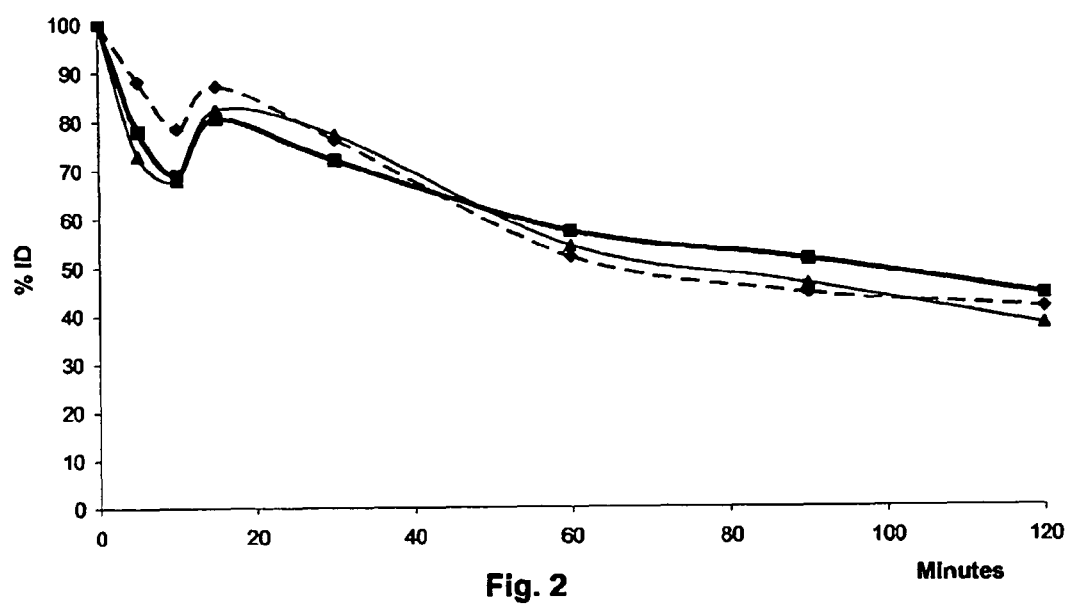
FIGS. 2-4 are graphs illustrating the stability in the blood circulation of assemblies of the invention.
Figure 3:
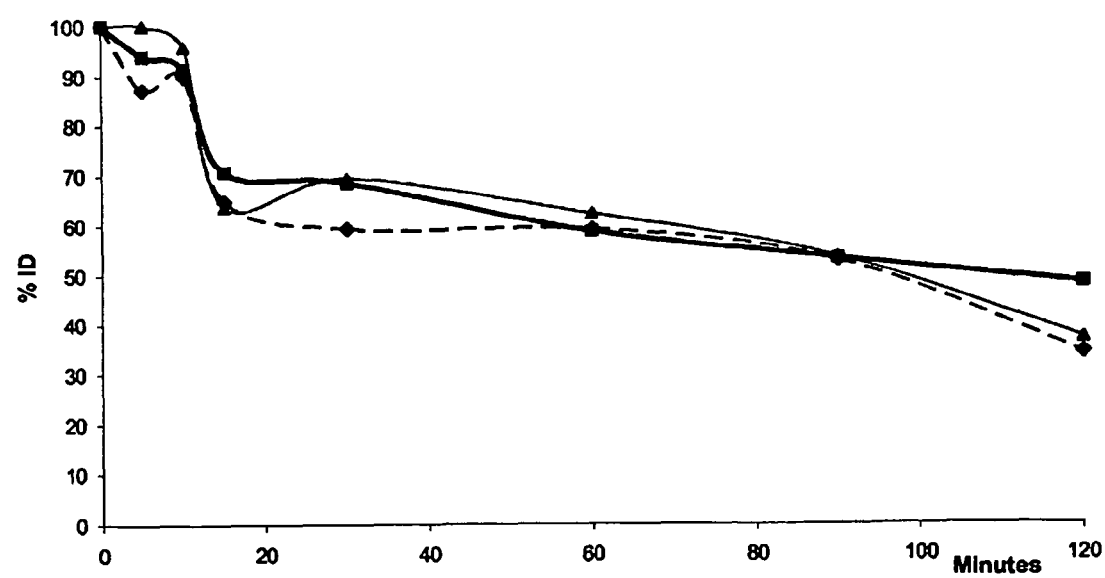
Figure 4:
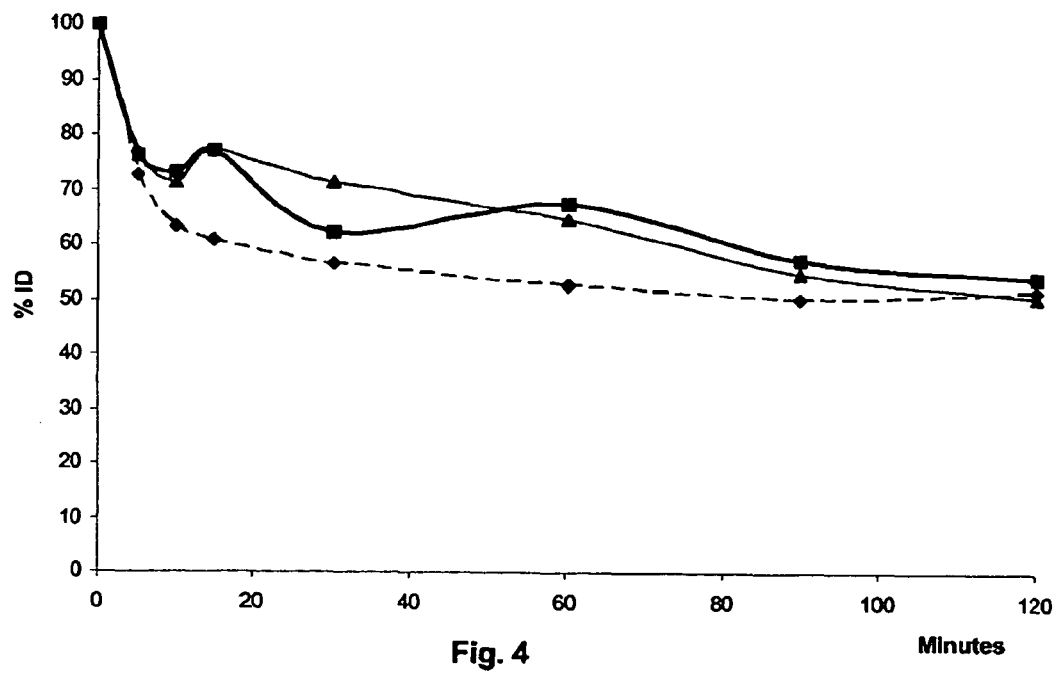

In the following, the liposomes preparations of examples 1, 2 and 3 are identified as L1 (mean size of 1.05 μm), L2 (mean size of 0.42 μm) and L3 (mean size of 0.22 μm), respectively, while the corresponding assembly preparations obtained as described in example 5 (i.e. by admixing each of said liposome preparation with the micelle preparation obtained according to example 4), are identified as A1, A2 and A3, respectively. The liposome and assembly preparations are then injected intravenously into six groups (three for the liposome and three for the assembly preparations) of 7 rats each (8 ml of suspension per kg of rat in the tail vein) and the concentration of iodine and gadolinium (blood elimination) for each injected preparation is determined at different instants by sacrificing one of the seven rats of each group at intervals of 5, 10, 15, 30, 60, 90 and 120 minutes. Gadolinium concentration at each time is determined as described in example 4 and is expressed as the percentage of the initial T1 and T2 values of the injected dose. Iodine concentration is determined by HPLC after treating aliquots of 500 µl of extracted blood with 100 µl of SDS (10 min, 65° C. under agitation) and 100 µl of 35% HClO$_4$ (10 min under centrifugation); the supernatant is then passed through a HPLC column (LiChrospher 10 RP-18, Merck; phase A: 10 mM potassium phosphate buffer, pH 6.0; phase B 30% MeOH, 70% phase A; 1 ml/min; detection UV: 240 nm); the iodine concentration is expressed as the percentage of the initial iodine concentration in the injected dose. FIGS. 2-4 show the graphs of elimination from blood of iodine (lines with rhombi) and of gadolinium (T1, lines with squares; T2, lines with triangles), for assembly preparations A1, A2 and A3, respectively.

Figure 5:
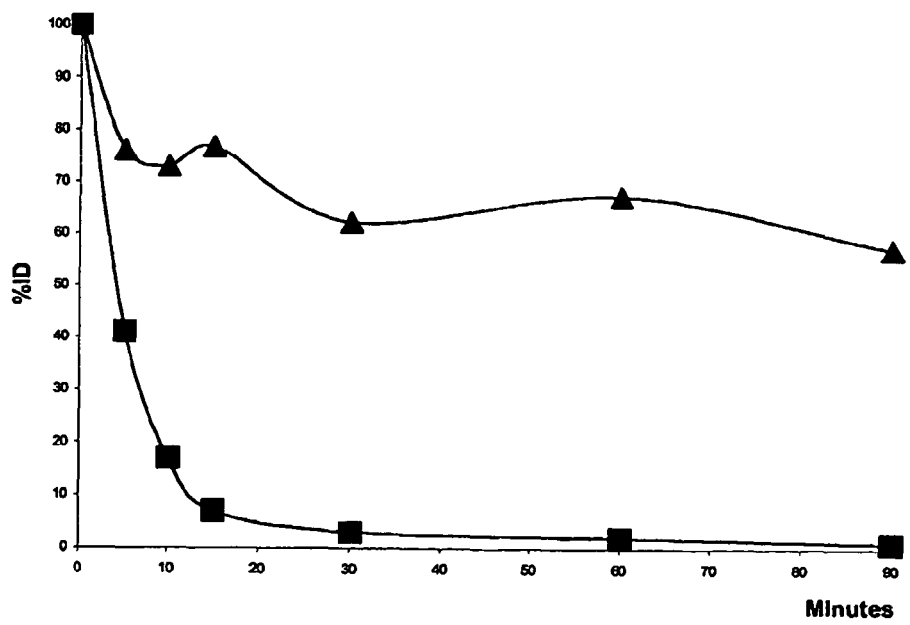

As inferable from said figures, assembly preparations A1, A2, and A3 have a substantially similar variation of iodine and gadolinium concentration vs. time, showing that the preparations follow a substantially similar blood elimination kinetic and that the assembly is stable when injected in the blood circulation (no separation between iodine-containing liposomes and gadolinium-containing micelles). On the contrary, as shown in FIGS. 5-7 (which illustrate the iodine variation in time for preparations A1-L1, A2-L2 and A3-L3, respectively), liposome preparations L1, L2 and L3 (lower lines with squares) show a rather faster kinetic of elimination from blood, as compared to the respective assemblies A1, A2 and A3 (upper lines with triangles), thus indicating that the micellar layer surrounding the liposomes acts as a kind of "stealth" barrier for the liposomes, allowing to increase their respective residence times in the blood circulation.

Example 10

In Vitro MR Imaging of Targeted Assemblies a. Preparation of the Assembly with Biotinylated Micelles A liposome suspension is prepared according to the procedure of Example 1.

A micellar suspension is prepared according to the procedure of Example 4, by dispersing 200 mg of Gd-complex, 150 mg of DSPE-PEG2000 and 50 mg of biotinated DSPE-PEG2000 in 10 ml of distilled water.

40 ml of the liposomal preparation are added to 5.25 ml of the micellar suspension under agitation (magnetic stirrer) and kept under stirring for 3 hours. Afterwards, the suspension is centrifuged for 30 minutes at 25,000 g, the liposome-micelle assemblies are recovered from the pellets of the centrifuged suspension (discarding the supernatant), and then suspended in a volume of PBS to a total volume of 35 ml.

The relatively high values of relaxation times T1 (1800 ms) and T2 (2000 ms) measured in the discarded supernatant phase allow the estimate that gadolinium is substantially absent from this phase and that the substantial totality of micelles are thus bound to the liposomes.

b. Preparation of the Neutravidin® Substrate

For the evaluation of the imaging efficacy of the assembly of the invention, two cartridges of hollow fibers (Minikros M11 260 01 P, polysulfonic membrane, from Spectrum Laboratories Inc.) are employed, to simulate the vascularized structure of a tumor. Details of the cartridge are as follows:

Fibers length: 12.2 cm; Total length: 18.5 cm; Diameter of the cartridge tube: 1.88 cm; Total useful surface: 615 cm$^2$; Fiber diameter: 0.05 cm; Internal volume of fiber: 0.024 cm$^3$; Internal surface of fiber: 1.92 cm$^2$.

Imaging Assay

A first cartridge (A, control) is filled with 25 ml of carbonate buffer (pH 9.8).

A second cartridge (B) is filled with a mixture of 4 ml of a 1 mg/ml Neutravidin® solution and 20 ml of a carbonate buffer (pH 9.8). The cartridge is left overnight at 4° C. and then rinsed three times with PBS buffer 0.1% (w/w) of Tween® 20. After rinsing, the cartridge is filled with 22 ml of the above assembly suspension, incubated for 24 hours at room temperature and then rinsed 10 times with 25 ml of PBS, until clear liquid results from washing.

The two cartridges are analyzed by means of a Philips Intera 1.5 T apparatus, with two different echo sequences, as detailed in the following tables 1 and 2. In the same tables, the relative intensity of the signal detected for both cartridges is given (expressed in relative arbitrary units).

TABLE 1

| Relative signal intensity Spin echo sequence: TR = 400 ms; TE = 20 ms | |
|---|---|
| Cartridge | Mean signal intensity |
| A | 512.68 |
| B | 1225.24 |

TABLE 2

| Relative signal intensity Gradient echo sequence: TR = 116 ms; TE = 29 ms; Flip angle: 80° | |
|---|---|
| Cartridge | Mean signal intensity |
| A | 339.92 |
| B | 1158.58 |

FIGS. 8a and 8b show the respective images corresponding to the values presented in table 2. From these figures, it can be appreciated the substantial imaging enhancement provided by a suspension containing a targeted assembly according to the invention in cartridge B, whereas a rather poor imaging of cartridge A is achieved.

Example 11

In Vivo MR Imaging of Targeted Assemblies

A liposome suspension comprising Gd-complex, SPC3, cholesterol and Ethyl-SPC3 in a molar ratio of 12.5/60/17.5/10 is prepared according to the procedure of example 8.

A micellar suspension is prepared according to the procedure of Example 4, by dispersing 200 mg of Gd-complex, 150 mg of DSPE-PEG2000 and 50 mg of biotinylated DSPE-PEG2000 in 10 ml of water.

40 ml of the liposomal preparation are added to 5.25 ml of the micellar suspension under agitation (magnetic stirrer) and kept under stirring for 3 hours. Afterwards, the suspension is centrifuged for 30 minutes at 25,000 g, the liposome-micelle assemblies are recovered from the bottom of the centrifuged suspension (discarding the supernatant), and then suspended in 0.4 M glucose to a final lipid concentration of 25 g/l. The assembly suspension is then incubated overnight with neutravidin at room temperature (biotin/neutravidin ratio: 20/1).

Imaging Assay

Two juxtaposed (right and left) VX2 tumors are implanted in the back of a rabbit. Fifteen days after implantation, 150 ug of Biot-β3 human antibody recognizing αVβ3 receptor expressed on endothelial cells (Chemicon International Inc.) is injected intravenously. 24 hours afterwards, the assembly preparations (3 ml/kg of rabbit) are injected and eight hours later the rabbit is subjected to MRI. A clear visualization of the two tumors is observed.

The invention claimed is:

1. A composition for diagnostic or therapeutic use which comprises an assembly comprising:
   a) a liposome comprising a first amphiphilic compound bearing a first overall net charge, said liposome having a boundary envelope with a respective inner and an outer surface, said envelope defining an internal portion thereof; and
   b) a plurality of micelles comprising: (i) a second amphiphilic compound; and (ii) an image enhancing compound; said second amphiphilic compound bearing a second overall net charge opposite in sign to said first net charge; said micelles being associated with the outer surface of the envelope of said liposome through a substantially electrostatic interaction.

2. A composition according to claim 1 wherein said second amphiphilic compound is a polymeric compound.

3. A composition according to claim 2 wherein said amphiphilic polymeric compound is a polymeric surfactant or a phospholipid bearing a hydrophilic polymeric moiety.

4. A composition according to claim 1 wherein said image enhancing compound is a MRI responsive compound.

5. A composition according to claim 4 wherein said MRI responsive compound is a paramagnetic metal ion complexed by a chelating molecule comprising a lipophilic moiety.

6. A composition according to claim 5 wherein said paramagnetic ion is selected from the group consisting of chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III).

7. A composition according to claim 5 wherein said chelating molecule is an amphipatic chelating agent comprising a chelating hydrophilic portion and a lipophilic portion.

8. A composition according to claim 7 wherein said chelating hydrophilic portion is a residue of a chelating acid selected from the group consisting of diethylenetriamine pentaacetic acid (DTPA), 1,4,7,10-tetraazacyclododecane-1,4,7,10-tetraacetic acid (DOTA), benzo-DOTA, dibenzo-DOTA, 1,4,7,-tricarboxymethyl 1,4,7,10 teraazacyclododecane triacetic acid (DO3A), 1,4,7,10-tetraazacyclo-dodecan-1-(2-hydroxypropyl)-4,7,10-triacetic acid (HP-DO3A), ethylenediamine-tetraacetic acid (EDTA), 1,4,8,11-tetraazacyclotetradecane-1,4,8,11-tetraacetic acid (TETA), benzo-TETA, ethylenebis-(2-hydroxy-phenylglycine) (EHPG), 5-Cl-EHPG, 5Br-EHPG, 5-Me-EHPG, 5t-Bu-EHPG, and Ssec-Bu-EHPG, benzodiethylenetriamine pentaacetic acid (benzo-DTPA), dibenzo-DTPA, phenyl-DTPA, diphenyl-DTPA, benzyl-DTPA, dibenzyl DTPA, bis-2 (hydroxybenzyl)-ethylene-diaminediacetic acid (HBED), 1,4,7-triazacyclo-nonane N,N',N"-triacetic acid (NOTA), benzo-NOTA, 1,4,7,10-tetraazacyclo-dodecane-1,4,7,10-tetra(methyl tetraacetic acid) (DOTMA), benzo-DOTMA, 1,4,8,11-tetraazacyclotetradecane-1,4,8,11-(methyl tetraacetic acid) (TETMA), benzo-TETMA, derivatives of 1,3-propylenediaminetetraacetic acid (PDTA), derivatives of triethylenetetraaminehexaacetic acid (TTHA), derivatives of 1,5,10-N,N',N"-tris(2,3-dihydroxybenzoyl)-tricatecholate (LICAM), and derivatives of 1,3,5-N,N',N"-tris(2,3-dihydroxybenzoyl) aminomethylbenzene (MECAM).

9. A composition according to claim 7 wherein said lipophilic portion is selected from the group consisting of a residue of a ($C_1$-$C_{24}$) alcohol, an aromatic alcohol, a ($C_1$-$C_{24}$) alkyl linear aliphatic amine, an aromatic amine, or mixtures thereof.

10. A composition according to claim 9 wherein said lipophilic portion is a residue of n-decyl alcohol, lauryl alcohol, myristyl alcohol, cetyl alcohol, n-octadecyl alcohol, benzyl alcohol, mono-, di- or tri-($C_1$-$C_4$)alkyl-phenyl alcohols, n-decyl amine, n-dodecyl amine, n-tetradecyl amine, n-hexadecyl amine, n-octadecyl amine, benzyl amine, mono-, di- or tri-($C_1$-$C_4$)alkyl-phenyl amine, or mixtures thereof.

11. A composition according to claim 5 wherein said MRI responsive compound is [10-[2-(dioctadecylamino)-2-oxoethyl]-1,4,7,10-tetraazacyclododecane-1,4,7-triacetate (3-)] Gadolinium.

12. A composition according to claim 1, wherein said micelles further comprises a targeting ligand.

13. A composition according to claim 1 wherein said liposome further comprises a therapeutic agent.

14. A composition according to claim 1 wherein said positively charged amphiphilic compound is selected from the group consisting of mono or di-esters of ethylphosphatidylcholine with or two fatty acid; alkylammonium salts comprising at least one ($C_{10}$-$C_{20}$), alkyl chain; tertiary or quaternary ammonium salts comprising one or two ($C_{10}$-$C_{20}$) acyl chain linked to the N-atom through a ($C_3$-$C_6$) alkylene bridge; and mixtures thereof.

15. A composition according to claim 1 wherein said negatively charged compound is selected from the group consisting of fatty acid di-ester of phophatidylserine, fatty acid di-ester of phosphatidic acid, fatty acid di-ester of phosphatidylglycerol, fatty acid di-ester of phosphatidylinositol, polytheyleneglycol-modified fatty acid di-ester of phosphatidylethanolamine, bile acid salts, ($C_{12}$-$C_{24}$) fatty acid salts, and mixtures thereof.

16. A composition according to claim 1 wherein said micelles further comprise an amphiphilic polymeric compound.

17. A method for preparing an assembly according to claim 1, which comprises admixing a preparation comprising a liposome or a precursor thereof with a preparation comprising a micelle or a precursor thereof to be associated to said liposome.

* * * * *